United States Patent
Finan et al.

(10) Patent No.: US 10,126,311 B2
(45) Date of Patent: *Nov. 13, 2018

(54) METHODS AND COMPOSITIONS FOR DETECTING ENDOMETRIAL OR OVARIAN CANCER

(71) Applicant: UNIVERSITY OF SOUTH ALABAMA, Mobile, AL (US)

(72) Inventors: Michael A. Finan, Mobile, AL (US); Rodney P. Rocconi, Mobile, AL (US); Lewis K. Pannell, Mobile, AL (US)

(73) Assignee: UNIVERSITY OF SOUTH ALABAMA, Mobile, AL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/709,147

(22) Filed: May 11, 2015

(65) Prior Publication Data

US 2015/0241453 A1    Aug. 27, 2015

Related U.S. Application Data

(60) Continuation of application No. 13/890,098, filed on May 8, 2013, now abandoned, which is a division of application No. 13/487,026, filed on Jun. 1, 2012, now Pat. No. 8,455,624.

(60) Provisional application No. 61/520,108, filed on Jun. 3, 2011, provisional application No. 61/614,347, filed on Mar. 22, 2012.

(51) Int. Cl.
*G01N 33/573* (2006.01)
*G01N 33/68* (2006.01)
*G01N 33/574* (2006.01)

(52) U.S. Cl.
CPC ... *G01N 33/6893* (2013.01); *G01N 33/57411* (2013.01); *G01N 2333/76* (2013.01); *G01N 2560/00* (2013.01); *G01N 2800/56* (2013.01); *G01N 2800/7028* (2013.01)

(58) Field of Classification Search
None
See application file for complete search history.

(56) References Cited

U.S. PATENT DOCUMENTS

| | | |
|---|---|---|
| 4,877,867 A | 10/1989 | Shalitin |
| 5,357,977 A | 10/1994 | Michels |
| 5,359,681 A | 10/1994 | Jorgenson et al. |
| 5,591,595 A | 1/1997 | Aken et al. |
| 5,658,743 A | 8/1997 | Imam et al. |
| 6,265,551 B1 | 7/2001 | Duke-Cohan et al. |
| 7,435,415 B2 | 10/2008 | Gelber |
| 7,491,551 B2 | 2/2009 | Boehringer et al. |
| 7,910,372 B2 | 3/2011 | Ishihama |
| 7,939,635 B2 | 5/2011 | Stracke et al. |
| 8,119,147 B2 | 2/2012 | Emery et al. |
| 2008/0038754 A1 | 2/2008 | Farias-Eisner et al. |
| 2009/0170208 A1* | 7/2009 | Fung ............ G01N 33/5091 436/64 |
| 2009/0230325 A1 | 9/2009 | Tsao et al. |
| 2010/0047812 A1 | 2/2010 | Van Eyk et al. |
| 2010/0279382 A1 | 11/2010 | Aebersold et al. |
| 2011/0262470 A1* | 10/2011 | Hakansson .......... C07K 14/765 424/185.1 |

FOREIGN PATENT DOCUMENTS

WO    WO 01/36977 A2    5/2001

OTHER PUBLICATIONS

Dzeranov et al, RU2360924, published 2009, only WIPO publication as cited in the rejection.*
Aebersold et al., "Mass spectrometry in proteomics." Chem Rev. 2001. 101(2):269-295.
Aebersold, "A mass spectrometric journey into protein and proteome research." J Am Soc Mass Spectrom. 2003. 14(7):685-695.
Aebersold et al., "Mass spectrometry-based proteomics." Nature. 2003. 422(6928):198-207.
Aebersold et al., Trends Biotechnol. 2002. 20:S1-2.
Aebersold, "Quantitative proteome analysis: methods and applications." J Infect Dis. 2003. 187(Suppl 2):S315-320.
Bao, J., "Capillary electrophoretic immunoassays." Chromatogr. B. Biomed. Sci. 1997. 699(1-2):463-80.
Chelius et al., J Proteome Res. 2002. 1:317-323.
David et al., Electrophoresis. 1999. 20:3551-67.
Diamandis, E. P., Mass spectrometry as a diagnostic and a cancer biomarker discovery tool, *Molecular & Cellular Proteomics*, 3:367-378.
Flory et al., "Advances in quantitative proteomics using stable isotope tags." Trends Biotechnol. 2002. 20:S23-29.
Goodlett et al., Anal Chem. 2000. 72:1112-1118.
Hallab, et al., In vitro Reactivity to Implant Metals Demonstrates a Person Dependent Association with both T-Cell and B-Cell Activation, *J Biomed Mater Res A*, Feb. 2010; 92(2):667-682.
Jemal et al., "Cancer statistics." CA Cancer J Clin. 2009. 59(4):225-49.
Kinter, "Protein Sequencing and Identification Using Tandem Mass Spectrometry." John Wiley & Sons, New York. 2000.
Kohler et al., Nature. 1975. 256:495.
Kong, et al., Preparation of specific monoclonal antibodies against chelated copper ions, *Biol Trace Elem Res.*, Mar. 2012; 145(3):388-395.
Liu, et al., Preparation and characterization of monoclonal antibody specific for copper-chelate complex, *J Immunol Methods.*, Jan. 31, 2013; 387(1-2):228-236.
Parra et al., J Vasc Surg. 1998. 28:669-675.
Patterson et al., "Proteomics: the first decade and beyond." Nat Genet. 2003. 33 Suppl:311-323.

(Continued)

*Primary Examiner* — Lei Yao
(74) *Attorney, Agent, or Firm* — Knobbe, Martens, Olson & Bear LLP

(57) ABSTRACT

Some embodiments of the present invention relate to methods and compositions for assessing the absence, presence, progression, or stage of cancer. In particular, methods and compositions for detecting endometrial cancer or ovarian cancer are provided.

12 Claims, 13 Drawing Sheets

Specification includes a Sequence Listing.

(56) References Cited

OTHER PUBLICATIONS

Quinlan et al., "Biochemical Properties and Therapeutic Potential." Hepatology. 2005. 41(6):1211-1219.

Rongen et al., "Liposomes and immunoassays." J Immunol Methods. 1997. 204(2):105-133.

Sackett et al., "Clinical Epidemiology: A Basic Science for Clinical Medicine." Little Brown and Co., 1985. pp. 106-107.

Schmalzing et al., "Capillary electrophoresis based immunoassays: a critical review." Electrophoresis. 1997. 18(12-13):2184-93.

Self et al., "Advances in immunoassay technology." Curr Opin Biotechnol. 1996. 7(1):60-65.

Tang et al., J Am Soc Mass Spectrom. 2004. 15:1416-1423.

Tao et al., "Advances in quantitative proteomics via stable isotope tagging and mass spectrometry." Curr Opin Biotechnol. 2003. 14(1):110-118.

Tibshirani, "Regression Shrinkage and Selection via the Lasso." J Roy Statist Soc Ser B. 1996. 58(1):267-288.

Vaitukaitis et al., J Clin Endocrinol Metab. 1971. 33:988-991.

Wiener et al., Anal Chem. 2004. 76:6085-6096.

Yang, et al., Detection of antibodies against corrosion products in patients after Co—Cr total joint replacements, *J Biomed Mater Res.*, Nov. 1994; 28(11):1249-1258.

Yasui et al., "A data-analytic strategy for protein biomarker discovery: profiling of high dimensional proteomic data for cancer detection." Biostatistics. 2003. 4(3):449-63.

Yates et al., "Automated protein identification using microcolumn liquid chromatography-tandem mass spectrometry." Methods Mol Biol. 1999. 112:553-569.

Yates, "Mass spectrometry and the age of the proteome." Mass Spect. 1998. 33(1):1-19.

Zhang, et al., Development of ELISA for detection of mercury based on specific monoclonal antibodies against mercury-chelate, *Biol Trace Elem Res.*, Dec. 2011; 144(1-3):854-864.

Zhu et al., J of Biomedicine and Biotech. 2010. Article ID: 840518 (6 pages).

Zhu, et al., Preparation of specific monoclonal antibodies (MAbs) against heavy metals: MAbs that recognize chelated cadmium ions, *J Agric Food Chem.*, Sep. 19, 2007; 55(19):7648-7653.

International Search Report and Written Opinion of the International Searching Authority dated Feb. 1, 2013, for International Application No. PCT/US2012/040566 filed Jun. 1, 2012.

\* cited by examiner

MS/MS Fragmentation of LVAASQAALGL
Found in gi|4502027, serum albumin preproprotein [Homo sapiens]

Match to Query 54: 1066.516214 from (534.265383,2+) index(64)
Title: es_375p_3.1941.1941.2.dta
Data file 1066.5090.mgf1

Click mouse within plot area to zoom in by factor of two about that point
Or, [Plot from] [150] to [1050] Da [Full range]
Label all possible matches ○   Label matches used for scoring ⊙

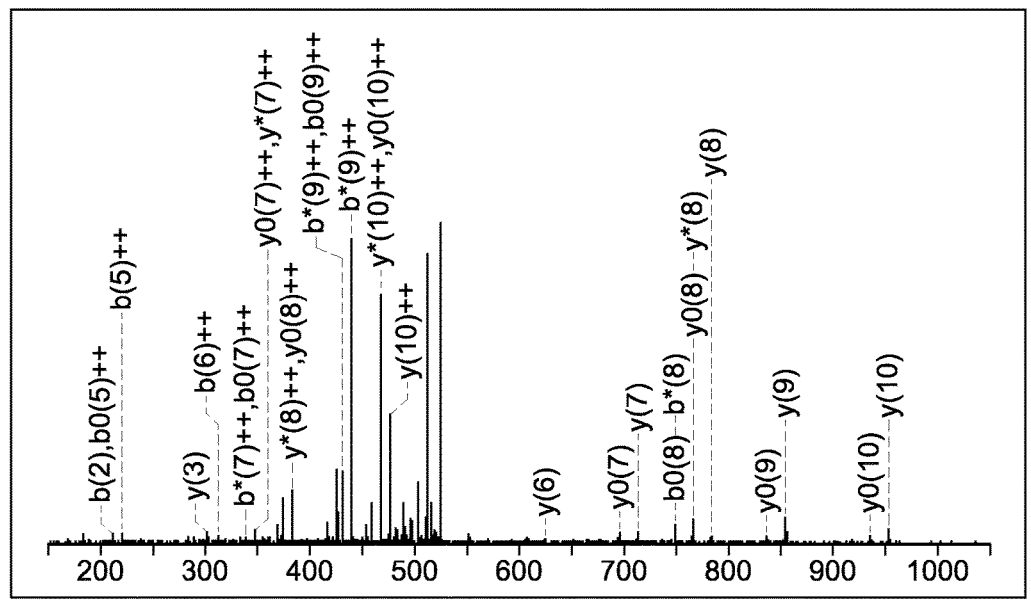

Monoisotopic mass of neutral peptide Mr (calc): 1066.5110
Variable modifications:
Q6: Iron (ACDEFGHIKLMNPQRSTVWY)
Ions Score: 55  Expect: 0.0076
Matches: 35/80 fragment ions using 36 most intense peaks   (help)

*FIG. 10*

MS/MS Fragmentation of AVMDDFAAFVEK
Found in gi|4502027, serum albumin preproprotein [Homo sapiens]

Match to Query 41: 1395.551004 from (698.782778,2+) index(31)
Title: f290p_3.3828.3838.2.dta
Data file 1395.5430.mgf1

Click mouse within plot area to zoom in by factor of two about that point
Or, [Plot from] [100] to [1500] Da [Full range]
Label all possible matches ○   Label matches used for scoring ⊙

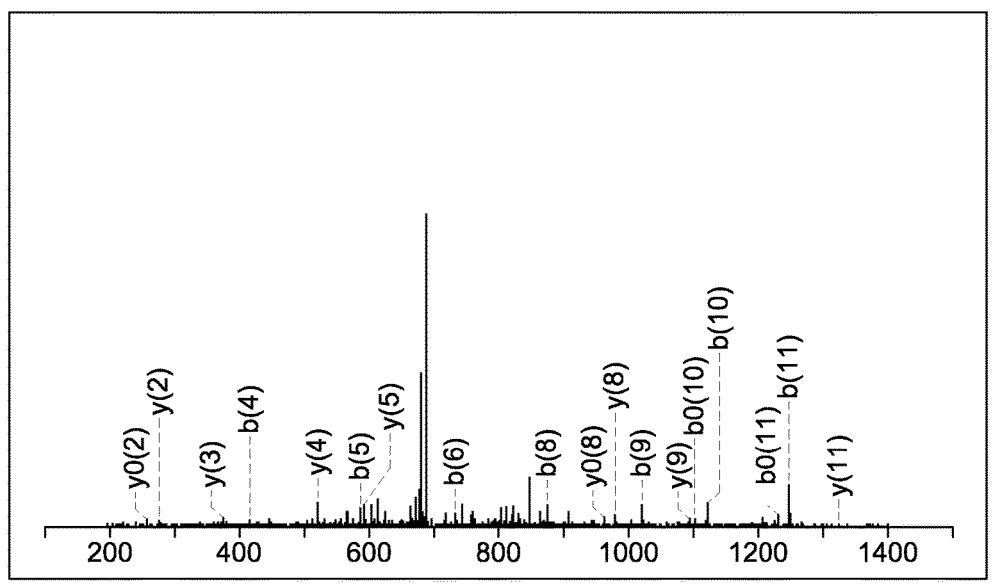

Monoisotopic mass of neutral peptide Mr (calc): 1395.5468
Variable modifications:
D5: Iron (ACDEFGHIKLMNPQRSTVWY)
Ions Score: 52  Expect: 0.025
Matches: 18/102 fragment ions using 36 most intense peaks  (help)

*FIG. 11*

MS/MS Fragmentation of VFDEFKPLVEEPQNLIK
Found in gi|4502027, serum albumin preproprotein [Homo sapiens]

Match to Query 160: 2098.020364 from (1050.17458,2+) index(159)
Title: sp296b_2.3616.3616.2.dta
Data file 2098.0061.mgfl Click mouse within plot area to zoom in by factor of two about that point
Or, [ Plot from ] [300      ] to [2000    ] Da      [ Full range ]
Label all possible matches ○  Label matches used for scoring ⊙

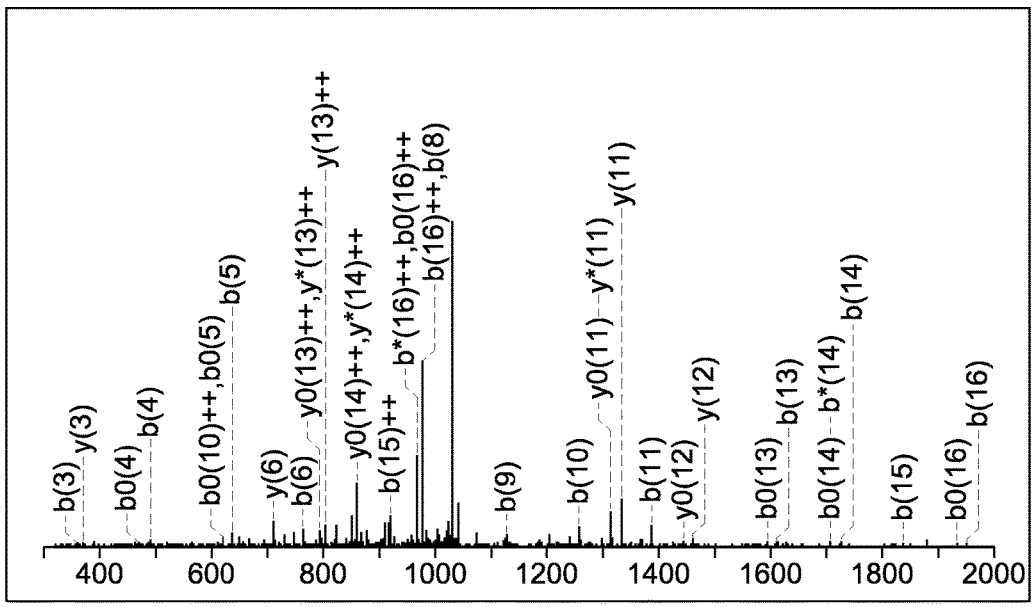

Monoisotopic mass of neutral peptide Mr (calc): 2098.0074
Variable modifications:
V9: Iron (ACDEFGHIKLMNPQRSTVWY)
Ions Score: 77  Expect: 0.00019
Matches: 35/166 fragment ions using 50 most intense peaks   (help)

*FIG. 12*

MS/MS Fragmentation of SHCIAEVENDEMPADLPSLAADFVESK
Found in gi|4502027, serum albumin preproprotein [Homo sapiens]

Match to Query 56: 2970.264543 from (991.095457,3+) index(49)
Title: es_375p_2.3329.3329.3.dta
Data file 2970.2400.mgf1

Click mouse within plot area to zoom in by factor of two about that point
Or, [Plot from] [200] to [2000] Da [Full range]
Label all possible matches ○   Label matches used for scoring ⊙

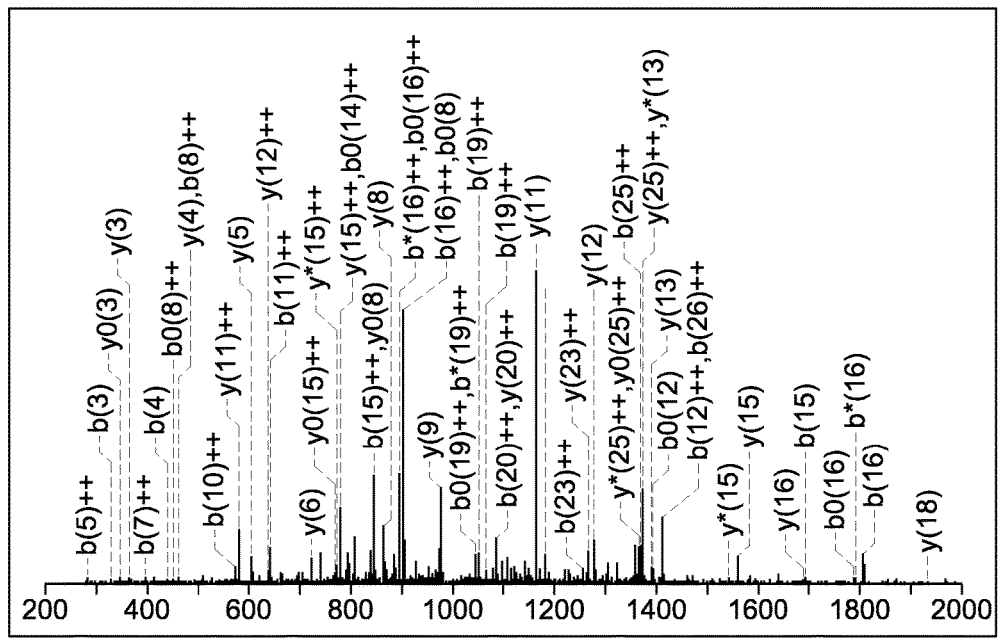

Monoisotopic mass of neutral peptide Mr (calc): 2970.2350
Variable modifications:
A5: Iron (ACDEFGHIKLMNPQRSTVWY)
Ions Score: 91  Expect: 1.5e-05
Matches: 55/294 fragment ions using 86 most intense peaks   (help)

*FIG. 13*

SEQUENCE LISTING

```
<160> NUMBER OF SEQ ID NOS: 33

<210> SEQ ID NO 1
<211> LENGTH: 11
<212> TYPE: PRT
<213> ORGANISM: Homo sapiens

<400> SEQUENCE: 1

Gln Leu Ser Glu Asp Gly Arg Gln Leu Arg Arg
 1               5                  10

<210> SEQ ID NO 2
<211> LENGTH: 11
<212> TYPE: PRT
<213> ORGANISM: Homo sapiens

<400> SEQUENCE: 2

Gly Glu Met Ser Gly Arg Leu Gly Pro Leu Lys
 1               5                  10

<210> SEQ ID NO 3
<211> LENGTH: 8
<212> TYPE: PRT
<213> ORGANISM: Homo sapiens

<400> SEQUENCE: 3

Gln Val Glu Val Lys Phe Gln Lys
 1               5

<210> SEQ ID NO 4
<211> LENGTH: 7
<212> TYPE: PRT
<213> ORGANISM: Homo sapiens
```

```
<400> SEQUENCE: 4

Asn Leu Leu Glu Lys Tyr Lys
1               5

<210> SEQ ID NO 5
<211> LENGTH: 9
<212> TYPE: PRT
<213> ORGANISM: Homo sapiens

<400> SEQUENCE: 5

Val Ala Gly Ala Ala Thr Pro Lys Lys
1               5

<210> SEQ ID NO 6
<211> LENGTH: 9
<212> TYPE: PRT
<213> ORGANISM: Homo sapiens

<400> SEQUENCE: 6

Ile Pro Ala Cys Ile Ala Gly Glu Arg
1               5

<210> SEQ ID NO 7
<211> LENGTH: 7
<212> TYPE: PRT
<213> ORGANISM: Homo sapiens

<400> SEQUENCE: 7

Leu Glu Lys Thr Val Pro Arg
1               5

<210> SEQ ID NO 8
<211> LENGTH: 7
<212> TYPE: PRT
<213> ORGANISM: Homo sapiens

<400> SEQUENCE: 8

Leu Glu Lys Thr Val Pro Thr
1               5

<210> SEQ ID NO 9
<211> LENGTH: 11
<212> TYPE: PRT
<213> ORGANISM: Homo sapiens

<400> SEQUENCE: 9

Leu Val Ala Ala Ser Gln Ala Ala Leu Gly Leu
1               5                   10

<210> SEQ ID NO 10
<211> LENGTH: 11
<212> TYPE: PRT
<213> ORGANISM: Homo sapiens

<400> SEQUENCE: 10

Leu Val Ala Ala Ser Gln Ala Ala Leu Gly Leu
1               5                   10

<210> SEQ ID NO 11
<211> LENGTH: 17
<212> TYPE: PRT
<213> ORGANISM: Homo sapiens

<400> SEQUENCE: 11
```

```
Val Phe Asp Glu Phe Lys Pro Leu Val Glu Glu Pro Gln Asn Leu Ile
1               5                   10                  15

Lys

<210> SEQ ID NO 12
<211> LENGTH: 15
<212> TYPE: PRT
<213> ORGANISM: Homo sapiens

<400> SEQUENCE: 12

Lys Val Pro Gln Val Ser Thr Pro Thr Leu Val Glu Val Ser Arg
1               5                   10                  15

<210> SEQ ID NO 13
<211> LENGTH: 8
<212> TYPE: PRT
<213> ORGANISM: Homo sapiens

<400> SEQUENCE: 13

Phe Tyr Ala Pro Glu Leu Leu Phe
1               5

<210> SEQ ID NO 14
<211> LENGTH: 12
<212> TYPE: PRT
<213> ORGANISM: Homo sapiens

<400> SEQUENCE: 14

Ala Val Met Asp Asp Phe Ala Ala Phe Val Glu Lys
1               5                   10

<210> SEQ ID NO 15
<211> LENGTH: 13
<212> TYPE: PRT
<213> ORGANISM: Homo sapiens

<400> SEQUENCE: 15

Lys Val Pro Gln Val Ser Thr Pro Thr Leu Val Glu Val
1               5                   10

<210> SEQ ID NO 16
<211> LENGTH: 10
<212> TYPE: PRT
<213> ORGANISM: Homo sapiens

<400> SEQUENCE: 16

Leu Val Asn Glu Val Thr Glu Phe Ala Lys
1               5                   10

<210> SEQ ID NO 17
<211> LENGTH: 11
<212> TYPE: PRT
<213> ORGANISM: Homo sapiens

<400> SEQUENCE: 17

Arg His Pro Tyr Phe Tyr Ala Pro Glu Leu Leu
1               5                   10

<210> SEQ ID NO 18
<211> LENGTH: 15
<212> TYPE: PRT
<213> ORGANISM: Homo sapiens

<400> SEQUENCE: 18
```

```
Glu Asp His Val Lys Leu Val Asn Glu Val Thr Glu Phe Ala Lys
 1               5                  10                  15

<210> SEQ ID NO 19
<211> LENGTH: 7
<212> TYPE: PRT
<213> ORGANISM: Homo sapiens

<400> SEQUENCE: 19

Tyr Leu Tyr Glu Ile Ala Arg
 1               5

<210> SEQ ID NO 20
<211> LENGTH: 10
<212> TYPE: PRT
<213> ORGANISM: Homo sapiens

<400> SEQUENCE: 20

Asn Tyr Ala Glu Ala Lys Asp Val Phe Leu
 1               5                  10

<210> SEQ ID NO 21
<211> LENGTH: 13
<212> TYPE: PRT
<213> ORGANISM: Homo sapiens

<400> SEQUENCE: 21

Ala Glu Val Ser Lys Leu Leu Val Thr Asp Leu Thr Lys
 1               5                  10

<210> SEQ ID NO 22
<211> LENGTH: 609
<212> TYPE: PRT
<213> ORGANISM: Homo sapiens

<400> SEQUENCE: 22

Met Lys Trp Val Thr Phe Ile Ser Leu Leu Phe Leu Phe Ser Ser Ala
 1               5                  10                  15

Tyr Ser Arg Gly Val Phe Arg Arg Asp Ala His Lys Ser Glu Val Ala
                20                  25                  30

His Arg Phe Lys Asp Leu Gly Glu Glu Asn Phe Lys Ala Leu Val Leu
            35                  40                  45

Ile Ala Phe Ala Gln Tyr Leu Gln Gln Cys Pro Phe Glu Asp His Val
        50                  55                  60

Lys Leu Val Asn Glu Val Thr Glu Phe Ala Lys Thr Cys Val Ala Asp
 65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190
```

```
Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
    210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
            245                 250                 255

Lys Leu Val Thr Asp Leu Thr Lys Val His Thr Glu Cys Cys His Gly
        260                 265                 270

Asp Leu Leu Glu Cys Ala Asp Asp Arg Ala Asp Leu Ala Lys Tyr Ile
            275                 280                 285

Cys Glu Asn Gln Asp Ser Ile Ser Ser Lys Leu Lys Glu Cys Cys Glu
        290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
            325                 330                 335

Lys Asp Val Cys Lys Asn Tyr Ala Glu Ala Lys Asp Val Phe Leu Gly
        340                 345                 350

Met Phe Leu Tyr Glu Tyr Ala Arg Arg His Pro Asp Tyr Ser Val Val
            355                 360                 365

Leu Leu Leu Arg Leu Ala Lys Thr Tyr Glu Thr Thr Leu Glu Lys Cys
    370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
            405                 410                 415

Glu Leu Phe Glu Gln Leu Gly Glu Tyr Lys Phe Gln Asn Ala Leu Leu
        420                 425                 430

Val Arg Tyr Thr Lys Lys Val Pro Gln Val Ser Thr Pro Thr Leu Val
            435                 440                 445

Glu Val Ser Arg Asn Leu Gly Lys Val Gly Ser Lys Cys Cys Lys His
450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
            485                 490                 495

Val Thr Lys Cys Cys Thr Glu Ser Leu Val Asn Arg Arg Pro Cys Phe
            500                 505                 510

Ser Ala Leu Glu Val Asp Glu Thr Tyr Val Pro Lys Glu Phe Asn Ala
        515                 520                 525

Glu Thr Phe Thr Phe His Ala Asp Ile Cys Thr Leu Ser Glu Lys Glu
        530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
            565                 570                 575

Ala Phe Val Glu Lys Cys Cys Lys Ala Asp Asp Lys Glu Thr Cys Phe
        580                 585                 590

Ala Glu Glu Gly Lys Lys Leu Val Ala Ala Ser Gln Ala Ala Leu Gly
    595                 600                 605
```

Leu

<210> SEQ ID NO 23
<211> LENGTH: 27
<212> TYPE: PRT
<213> ORGANISM: Homo sapiens

<400> SEQUENCE: 23

Ser His Cys Ile Ala Glu Val Glu Asn Asp Glu Met Pro Ala Asp Leu
1               5                   10                  15

Pro Ser Leu Ala Ala Asp Phe Val Glu Ser Lys
            20                  25

<210> SEQ ID NO 24
<211> LENGTH: 12
<212> TYPE: PRT
<213> ORGANISM: Homo sapiens

<400> SEQUENCE: 24

Ala Val Met Asp Asp Phe Ala Ala Phe Val Glu Lys
1               5                   10

<210> SEQ ID NO 25
<211> LENGTH: 13
<212> TYPE: PRT
<213> ORGANISM: Homo sapiens

<400> SEQUENCE: 25

Asp Val Phe Leu Gly Met Phe Leu Tyr Glu Tyr Ala Arg
1               5                   10

<210> SEQ ID NO 26
<211> LENGTH: 13
<212> TYPE: PRT
<213> ORGANISM: Homo sapiens

<400> SEQUENCE: 26

Asp Val Phe Leu Gly Met Phe Leu Tyr Glu Tyr Ala Arg
1               5                   10

<210> SEQ ID NO 27
<211> LENGTH: 21
<212> TYPE: PRT
<213> ORGANISM: Homo sapiens

<400> SEQUENCE: 27

Met Pro Cys Ala Glu Asp Tyr Leu Ser Val Val Leu Asn Gln Leu Cys
1               5                   10                  15

Val Leu His Glu Lys
            20

<210> SEQ ID NO 28
<211> LENGTH: 22
<212> TYPE: PRT
<213> ORGANISM: Homo sapiens

<400> SEQUENCE: 28

Val His Thr Glu Cys Cys His Gly Asp Leu Leu Glu Cys Ala Asp Asp
1               5                   10                  15

Arg Ala Asp Leu Ala Lys
            20

<210> SEQ ID NO 29

```
<211> LENGTH: 21
<212> TYPE: PRT
<213> ORGANISM: Homo sapiens

<400> SEQUENCE: 29

Gln Asn Cys Glu Leu Phe Glu Gln Leu Gly Glu Tyr Lys Phe Gln Asn
 1               5                  10                  15

Ala Leu Leu Val Arg
            20

<210> SEQ ID NO 30
<211> LENGTH: 22
<212> TYPE: PRT
<213> ORGANISM: Homo sapiens

<400> SEQUENCE: 30

Arg Met Pro Cys Ala Glu Asp Tyr Leu Ser Val Val Leu Asn Gln Leu
 1               5                  10                  15

Cys Val Leu His Glu Lys
            20

<210> SEQ ID NO 31
<211> LENGTH: 23
<212> TYPE: PRT
<213> ORGANISM: Homo sapiens

<400> SEQUENCE: 31

Leu Val Arg Pro Glu Val Asp Val Met Cys Thr Ala Phe His Asp Asn
 1               5                  10                  15

Glu Glu Thr Phe Leu Lys Lys
            20

<210> SEQ ID NO 32
<211> LENGTH: 27
<212> TYPE: PRT
<213> ORGANISM: Homo sapiens

<400> SEQUENCE: 32

Ser His Cys Ile Ala Glu Val Glu Asn Asp Glu Met Pro Ala Asp Leu
 1               5                  10                  15

Pro Ser Leu Ala Ala Asp Phe Val Glu Ser Lys
            20                  25

<210> SEQ ID NO 33
<211> LENGTH: 31
<212> TYPE: PRT
<213> ORGANISM: Homo sapiens

<400> SEQUENCE: 33

Ser His Cys Ile Ala Glu Val Glu Asn Asp Glu Met Pro Ala Asp Leu
 1               5                  10                  15

Pro Ser Leu Ala Ala Asp Phe Val Glu Ser Lys Asp Val Cys Lys
            20                  25                  30
```

METHODS AND COMPOSITIONS FOR DETECTING ENDOMETRIAL OR OVARIAN CANCER

RELATED APPLICATIONS

This application is a continuation of U.S. patent application Ser. No. 13/890,098 filed May 8, 2013, now abandoned which is a division of U.S. patent application Ser. No. 13/487,026 entitled "METHODS AND COMPOSITIONS FOR DETECTING ENDOMETRIAL OR OVARIAN CANCER" filed on Jun. 1, 2012, which claims the benefit of U.S. Provisional Application No. 61/614,347 entitled "METHODS AND COMPOSITIONS FOR DETECTING ENDOMETRIAL OR OVARIAN CANCER" filed on Mar. 22, 2012, and U.S. Provisional Application No. 61/520,108 entitled "IRON MODIFIED PEPTIDES AS BIOMARKERS OF GYNECOLOGIC MALIGNANCIES" filed on Jun. 3, 2011, the entire disclosures of which are incorporated herein by reference in their entireties.

REFERENCE TO SEQUENCE LISTING

The present application is being filed along with a Sequence Listing in electronic format. The Sequence Listing is provided as a file entitled SWFT_002C1.TXT, created May 11, 2015, which is approximately 12 KB in size. The information in the electronic format of the Sequence Listing is incorporated herein by reference in its entirety.

FIELD OF THE INVENTION

Some embodiments of the present invention relate to methods and compositions for assessing the absence, presence, progression, or stage of cancer. In particular, methods and compositions for detecting endometrial cancer or ovarian cancer are provided.

BACKGROUND OF THE INVENTION

Ovarian cancer is among the most lethal gynecologic malignancies in developed countries. In the United States, approximately 23,000 women are diagnosed with the disease and almost 14,000 women die from it each year. There are three main types of ovarian cancer: epithelial, germ cell, and sex cord stromal. About 90% of ovarian cancers start in the epithelium tissue, which is the lining on the outside of the ovary. This type of ovarian cancer is divided into serous, mucinous, endometrioid, clear cell, transitional and undifferentiated types. The risk of epithelial ovarian cancer increases with age, especially after the age of 50. Germ cell tumors account for about 5% of ovarian cancers. They begin in the egg-producing cells. This type of ovarian cancer can occur in women of any age, but about 80% are found in women under the age of 30. The main subtypes are teratoma, dysgerminoma, endodermal sinus tumor and choriocarcinoma. Sex cord stromal tumors, about 5% of ovarian cancers, grow in the connective tissue that holds the ovary together and makes estrogen and progesterone. Most are found in older women. Despite progress in cancer therapy, ovarian cancer mortality has remained virtually unchanged over the past two decades. Given the steep survival gradient relative to the stage at which the disease is diagnosed, early detection remains the most important factor in improving long-term survival of ovarian cancer patients.

Endometrial cancer is the most common gynecologic malignancy and accounts for about 13% of all malignancies occurring in women. There are about 34,000 cases of endometrial cancer diagnosed in the United States each year. All endometrial carcinomas arise from the glands of the lining of the uterus. Adenocarcinoma accounts for 75% of all endometrial carcinoma. Endometrial adenocarcinomas that contain benign or malignant squamous cells are known as adenocanthomas and adenosquamous carcinomas respectively and account for 30% of endometrial cancers. The remaining types of endometrial carcinoma have a poorer prognosis. About 3% have a clear cell carcinoma, and about 1% have a papillary carcinoma.

Currently, there are no convincing early detection approaches for endometrial and ovarian cancers. Although it is well established that some endometrial and ovarian tumors shed cytologically recognizable cells in routinely prepared Pap tests, it is clear that this approach rarely detects occult tumors. Accordingly, efforts to develop means of collecting biological samples that have high patient acceptability, good sensitivity for detecting early disease, and excellent specificity are needed.

SUMMARY OF THE INVENTION

Some embodiments of the methods and compositions provided herein include a method for assessing the presence, absence, progression or stage of cancer in a female subject. Some such embodiments include determining the level of at least one polypeptide or fragment thereof or the level of at least one nucleic acid encoding said at least one polypeptide or fragment thereof in a sample from said subject, wherein said at least one polypeptide is selected from the group consisting of a polypeptide comprising, consisting essentially of, or consisting of one of SEQ ID NOs.:9-33, or comprises, consists essentially of, or consists of an albumin protein fragment having a mass selected from the group consisting of about 2044, about 2098, about 2070, about 1013, about 1067, about 1639, about 999, about 1342, about 1396, about 1149, about 1405, about 1757, about 952, about 1169, about 1303, about 1623, about 1677, about 2403, about 2457, about 2413, about 2467, about 2541, about 2595, about 2559, about 2613, about 2720, about 2774, about 2916, about 2970, about 3362, about 3415 and about 1396.

In some embodiments, the sample is obtained from the cervix, the vagina, or the posterior vaginal fornix.

Some embodiments also include determining the level of at least two polypeptides or the level of at least two nucleic acids encoding said polypeptides or a fragment thereof, wherein the polypeptide is selected from the group consisting of a polypeptide comprising, consisting essentially of, or consisting of one of SEQ ID NOs.:9-33, or comprises, consists essentially of, or consists of an albumin protein fragment having a mass selected from the group consisting of about 2044, about 2098, about 2070, about 1013, about 1067, about 1639, about 999, about 1342, about 1396, about 1149, about 1405, about 1757, about 952, about 1169, about 1303, about 1623, about 1677, about 2403, about 2457, about 2413, about 2467, about 2541, about 2595, about 2559, about 2613, about 2720, about 2774, about 2916, about 2970, about 3362, about 3415 and about 1396.

Some embodiments also include determining the level of at least three polypeptides or the level of at least three nucleic acids encoding said polypeptides or a fragment thereof, wherein the polypeptide is selected from the group consisting of a polypeptide comprising, consisting essentially of, or consisting of one of SEQ ID NOs.:9-33, or comprises, consists essentially of, or consists of an albumin protein fragment having a mass selected from the group consisting of about 2044, about 2098, about 2070, about 1013, about 1067, about 1639, about 999, about 1342, about 1396, about 1149, about 1405, about 1757, about 952, about 1169, about 1303, about 1623, about 1677, about 2403, about 2457, about 2413, about 2467, about 2541, about 2595, about 2559, about 2613, about 2720, about 2774, about 2916, about 2970, about 3362, about 3415 and about 1396.

Some embodiments also include determining the level of at least five polypeptides or the level of at least five nucleic acids encoding said polypeptides or a fragment thereof, wherein the polypeptide is selected from the group consisting of a polypeptide comprising, consisting essentially of, or consisting of one of SEQ ID NOs.:9-33, or comprises, consists essentially of, or consists of an albumin protein fragment having a mass selected from the group consisting of about 2044, about 2098, about 2070, about 1013, about 1067, about 1639, about 999, about 1342, about 1396, about 1149, about 1405, about 1757, about 952, about 1169, about 1303, about 1623, about 1677, about 2403, about 2457, about 2413, about 2467, about 2541, about 2595, about 2559, about 2613, about 2720, about 2774, about 2916, about 2970, about 3362, about 3415 and about 1396.

Some embodiments also include comparing the level of at least one polypeptide or the level of a nucleic acid encoding the polypeptide in a sample from the subject with the level of at least one polypeptide or the level of a nucleic acid encoding the polypeptide in a sample from a subject without the cancer or with a reference level of the at least one polypeptide or of the nucleic acid encoding the polypeptide, wherein the reference level is known to be indicative of the presence or absence of the cancer.

In some embodiments, an increase in the level of said at least one polypeptide or fragment thereof or the level of said at least one nucleic acid encoding the polypeptide or a fragment thereof in a sample from said subject compared to the level of said at least one polypeptide or fragment thereof or the level of said at least one nucleic acid encoding said at least one polypeptide in a sample from said subject without cancer or compared to said reference level of the at least one polypeptide or of the nucleic acid encoding the polypeptide is indicative of the presence of the cancer in the subject.

In some embodiments, the cancer comprises endometrial cancer, wherein the polypeptide comprises, consists essentially of, or consists of an amino acid sequence selected from the group consisting of SEQ ID NOs.: 9-12 or SEQ ID NOs.: 24-33, or comprises, consists essentially of, or consists of an albumin protein fragment having a mass selected from the group consisting of about 1013, about 1067, about 1396, about 1623, about 1677, about 1639, about 2044, about 2098, about 2403, about 2457, about 2413, about 2467, about 2541, about 2595, about 2559, about 2613, about 2720, about 2774, about 2916, about 2970, about 3362, about 3415 and about 1396.

In some embodiments, the cancer comprises ovarian cancer, wherein the polypeptide comprises, consists essentially of, or consists of an amino acid sequence selected from the group consisting of SEQ ID NOs.: 11-21, or comprises, consists essentially of, or consists of an albumin protein fragment having a mass selected from the group consisting of about 2044, about 2098, about 2070, about 1639, about 999, about 1342, about 1396, about 1149, about 1405, about 1757, about 952, about 1169, and about 1303.

In some embodiments, at least a 3-fold increase in the level of the said at least one polypeptide or fragment thereof or the level of said at least one nucleic acid encoding the polypeptide or fragment thereof in a sample from said subject compared to the level of said at least one polypeptide or fragment thereof or the level of said at least one nucleic acid encoding the polypeptide or fragment thereof in a sample from said subject without cancer or compared to said reference level of the at least one polypeptide or of the nucleic acid encoding the polypeptide is indicative of the presence of the cancer in the subject.

In some embodiments, at least a 5-fold increase in the level of the said at least one polypeptide or fragment thereof or the level of said at least one nucleic acid encoding the polypeptide or fragment thereof in a sample from said subject compared to the level of said at least one polypeptide or fragment thereof or the level of said at least one nucleic acid encoding the polypeptide or fragment thereof in a sample from said subject without cancer or compared to said reference level of the at least one polypeptide or of the nucleic acid encoding the polypeptide is indicative of the presence of the cancer in the subject.

In some embodiments, at least a 10-fold increase in the level of the said at least one polypeptide or fragment thereof or the level of said at least one nucleic acid encoding the polypeptide or fragment thereof in a sample from said subject compared to the level of said at least one polypeptide or fragment thereof or the level of said at least one nucleic acid encoding the polypeptide or fragment thereof in a sample from said subject without cancer or compared to said reference level of the at least one polypeptide or of the nucleic acid encoding the polypeptide is indicative of the presence of the cancer in the subject.

In some embodiments, at least a 100-fold increase in the level of the said at least one polypeptide or fragment thereof or the level of said at least one nucleic acid encoding the polypeptide or fragment thereof in a sample from said subject compared to the level of said at least one polypeptide or fragment thereof or the level of said at least one nucleic acid encoding the polypeptide or fragment thereof in a sample from said subject without cancer or compared to said reference level of the at least one polypeptide or of the nucleic acid encoding the polypeptide is indicative of the presence of the cancer in the subject.

In some embodiments, determining the level of said at least one polypeptide or fragment thereof comprises performing an immunoassay or colorimetric assay.

In some embodiments, the immunoassay is selected from the group consisting of a Western blot, an enzyme linked immunoabsorbent assay (ELISA), and radioimmunoassay.

In some embodiments, determining the level of said at least one polypeptide or fragment thereof comprises mass spectrometry.

In some embodiments, determining the level of said at least one polypeptide or fragment thereof comprises applying said sample to a solid phase test strip or flow-through test strip comprising an agent which selectively binds to said at least one polypeptide or fragment thereof; and detecting said polypeptide bound to said agent on said solid phase test strip or flow-through test strip.

In some embodiments, the cancer is a non-cervical cancer of the gynecological tract.

In some embodiments, the cancer is selected from the group consisting of endometrial cancer, and ovarian cancer.

In some embodiments, the cancer is selected from the group consisting of endometrial hyperplasia, endometrial hyperplasia with atypia, and non-invasive endometrial cancer.

In some embodiments, the sample is obtained from a cervical pap specimen.

In some embodiments, the sample is substantially free of cells.

In some embodiments, the polypeptide comprises at least one residue associated with iron.

In some embodiments, the subject is human.

In some embodiments, the sample comprises an ex vivo sample.

Some embodiments of the methods and compositions provided herein include a kit for assessing the presence, absence, progression or stage of a cancer in a female subject comprising: (a) a suitable diluent for irrigating the uterine cavity of the subject; (b) a receptacle for collection of the diluted uterine fluid; and (c) an agent that selectively binds to at least one polypeptide or fragment thereof or a nucleic acid encoding said polypeptide or fragment thereof, wherein said polypeptide comprises, consists essentially of, or consists of a polypeptide selected from the group consisting of SEQ ID NOs.:9-33, or comprises, consists essentially of, or consists of an albumin protein fragment having a mass selected from the group consisting of about 2044, about 2098, about 2070, about 1013, about 1067, about 1639, about 999, about 1342, about 1396, about 1149, about 1405, about 1757, about 952, about 1169, about 1303, about 1623, about 1677, about 2403, about 2457, about 2413, about 2467, about 2541, about 2595, about 2559, about 2613, about 2720, about 2774, about 2916, about 2970, about 3362, about 3415 and about 1396.

Some embodiments also include at least three agents that each selectively bind to a different polypeptide or fragment thereof or a nucleic acid encoding said polypeptide or fragment thereof, wherein said polypeptide comprises, consists essentially of, or consists of a polypeptide selected from the group consisting of SEQ ID NOs.:9-33, or comprises, consists essentially of, or consists of an albumin protein fragment having a mass selected from the group consisting of about 2044, about 2098, about 2070, about 1013, about 1067, about 1639, about 999, about 1342, about 1396, about 1149, about 1405, about 1757, about 952, about 1169, about 1303, about 1623, about 1677, about 2403, about 2457, about 2413, about 2467, about 2541, about 2595, about 2559, about 2613, about 2720, about 2774, about 2916, about 2970, about 3362, about 3415 and about 1396.

Some embodiments also include at least five agents that each selectively bind to a different polypeptide or fragment thereof or a nucleic acid encoding said polypeptide or fragment thereof, wherein said polypeptide comprises, consists essentially of, or consists of a polypeptide selected from the group consisting of SEQ ID NOs.:9-33, or comprises, consists essentially of, or consists of an albumin protein fragment having a mass selected from the group consisting of about 2044, about 2098, about 2070, about 1013, about 1067, about 1639, about 999, about 1342, about 1396, about 1149, about 1405, about 1757, about 952, about 1169, about 1303, about 1623, about 1677, about 2403, about 2457, about 2413, about 2467, about 2541, about 2595, about 2559, about 2613, about 2720, about 2774, about 2916, about 2970, about 3362, about 3415 and about 1396.

In some embodiments, the agent comprises an antibody or fragment thereof.

Some embodiments of the methods and compositions provided herein include a kit comprising an agent which selectively binds to at least one polypeptide or fragment thereof, wherein the polypeptide comprises, consists essentially of, or consists of a polypeptide selected from the group consisting of SEQ ID NOs.:9-33, or comprises, consist essentially of, consists of an albumin protein fragment having a mass selected from the group consisting of about 2044, about 2098, about 2070, about 1013, about 1067, about 1639, about 999, about 1342, about 1396, about 1149, about 1405, about 1757, about 952, about 1169, about 1303, about 1623, about 1677, about 2403, about 2457, about 2413, about 2467, about 2541, about 2595, about 2559, about 2613, about 2720, about 2774, about 2916, about 2970, about 3362, about 3415 and about 1396, wherein said agent is attached to a solid support.

In some embodiments, a plurality of agents that bind to different polypeptides or fragments thereof which comprise, consist essentially of, or consist of an amino acid sequence selected from the group consisting of SEQ ID NOs.:9-33, or which comprise, consist essentially of, or consist of an albumin protein fragment having a mass selected from the group consisting of about 2044, about 2098, about 2070, about 1013, about 1067, about 1639, about 999, about 1342, about 1396, about 1149, about 1405, about 1757, about 952, about 1169, about 1303, about 1623, about 1677, about 2403, about 2457, about 2413, about 2467, about 2541, about 2595, about 2559, about 2613, about 2720, about 2774, about 2916, about 2970, about 3362, about 3415 and about 1396, are attached to said solid support.

In some embodiments, the solid support comprises a solid phase test strip or flow-through strip.

Some embodiments also include a detectable agent which selectively binds to said polypeptide.

Some embodiments of the methods and compositions provided herein include a kit comprising an agent which selectively binds to at least one nucleic acid encoding a polypeptide or fragment thereof, wherein said polypeptide comprises, consists essentially of, or consists of an amino acid sequence selected from the group consisting of SEQ ID NOs.:9-33 or a fragment thereof, or encodes an albumin protein fragment comprising, consisting essentially of, or consisting of a mass selected from the group consisting about 2044, about 2098, about 2070, about 1013, about 1067, about 1639, about 999, about 1342, about 1396, about 1149, about 1405, about 1757, about 952, about 1169, about 1303, about 1623, about 1677, about 2403, about 2457, about 2413, about 2467, about 2541, about 2595, about 2559, about 2613, about 2720, about 2774, about 2916, about 2970, about 3362, about 3415 and about 1396, wherein said agent is attached to a solid support.

Some embodiments also include an agent that selectively binds to at least one polypeptide or nucleic acid encoding a polypeptide, wherein said polypeptide is selected from the group consisting of SEQ ID NOs.:9-33, or is an albumin protein fragment having a mass selected from the group consisting of about 2044, about 2098, about 2070, about 1013, about 1067, about 1639, about 999, about 1342, about 1396, about 1149, about 1405, about 1757, about 952, about 1169, about 1303, about 1623, about 1677, about 2403, about 2457, about 2413, about 2467, about 2541, about 2595, about 2559, about 2613, about 2720, about 2774, about 2916, about 2970, about 3362, about 3415 and about 1396.

In some embodiments, a plurality of agents that bind to nucleic acids encoding different polypeptides or fragments thereof which comprise, consist essentially of, or consist of a nucleic acid encoding an amino acid sequence selected from the group consisting of an amino acid sequence selected from the group consisting of SEQ ID NOs.:9-33 or a fragment thereof, or encoding an albumin protein fragment which comprises, consists essentially of, or consists of a mass selected from the group consisting of about 2044, about 2098, about 2070, about 1013, about 1067, about 1639, about 999, about 1342, about 1396, about 1149, about 1405, about 1757, about 952, about 1169, about 1303, about 1623, about 1677, about 2403, about 2457, about 2413, about 2467, about 2541, about 2595, about 2559, about 2613, about 2720, about 2774, about 2916, about 2970, about 3362, about 3415 and about 1396, are attached to said solid support.

In some embodiments, the solid support comprises a solid phase test strip or flow-through strip.

Some embodiments also include a detectable agent which selectively binds to said polypeptide.

In some embodiments, the polypeptide comprises at least one residue associated with iron.

In some embodiments, the cancer is selected from the group consisting of endometrial cancer, and ovarian cancer.

In some embodiments, the cancer is selected from the group consisting of endometrial hyperplasia, endometrial hyperplasia with atypia, and non-invasive endometrial cancer.

An isolated polypeptide consisting essentially of an amino acid sequence selected from the group consisting of SEQ ID NOs.:9-33 or a fragment thereof, or an albumin protein fragment having a mass selected from the group consisting of about 2044, about 2098, about 2070, about 1013, about 1067, about 1639, about 999, about 1342, about 1396, about 1149, about 1405, about 1757, about 952, about 1169, about 1303, about 1623, about 1677, about 2403, about 2457, about 2413, about 2467, about 2541, about 2595, about 2559, about 2613, about 2720, about 2774, about 2916, about 2970, about 3362, about 3415 and about 1396 wherein said polypeptide is differentially expressed in cancer.

An isolated nucleic acid encoding a polypeptide consisting essentially of an amino acid sequence selected from the group consisting of SEQ ID NOs.:9-33 or a fragment thereof, or encoding an albumin protein fragment having a mass selected from the group consisting of about 2044, about 2098, about 2070, about 1013, about 1067, about 1639, about 999, about 1342, about 1396, about 1149, about 1405, about 1757, about 952, about 1169, about 1303, about 1623, about 1677, about 2403, about 2457, about 2413, about 2467, about 2541, about 2595, about 2559, about 2613, about 2720, about 2774, about 2916, about 2970, about 3362, about 3415 and about 1396, wherein said polypeptide is differentially expressed in cancer.

An isolated polypeptide consisting of an amino acid sequence selected from the group consisting of SEQ ID NOs.:9-33 or a fragment thereof, or an albumin protein fragment having a mass selected from the group consisting of about 2044, about 2098, about 2070, about 1013, about 1067, about 1639, about 999, about 1342, about 1396, about 1149, about 1405, about 1757, about 952, about 1169, about 1303, about 1623, about 1677, about 2403, about 2457, about 2413, about 2467, about 2541, about 2595, about 2559, about 2613, about 2720, about 2774, about 2916, about 2970, about 3362, about 3415 and about 1396, wherein said polypeptide is differentially expressed in cancer.

An isolated nucleic acid encoding a polypeptide consisting of an amino acid sequence selected from the group consisting of SEQ ID NOs.:9-33 or a fragment thereof, or encoding an albumin protein fragment having a mass selected from the group consisting of about 2044, about 2098, about 2070, about 1013, about 1067, about 1639, about 999, about 1342, about 1396, about 1149, about 1405, about 1757, about 952, about 1169, about 1303, about 1623, about 1677, about 2403, about 2457, about 2413, about 2467, about 2541, about 2595, about 2559, about 2613, about 2720, about 2774, about 2916, about 2970, about 3362, about 3415 and about 1396, wherein said polypeptide is differentially expressed in cancer.

An isolated agent that selectively binds to an isolated polypeptide consisting essentially of an amino acid sequence selected from the group consisting of SEQ ID NOs.:9-33 or a fragment thereof, or an albumin protein fragment having a mass selected from the group consisting of about 2044, about 2098, about 2070, about 1013, about 1067, about 1639, about 999, about 1342, about 1396, about 1149, about 1405, about 1757, about 952, about 1169, about 1303, about 1623, about 1677, about 2403, about 2457, about 2413, about 2467, about 2541, about 2595, about 2559, about 2613, about 2720, about 2774, about 2916, about 2970, about 3362, about 3415 and about 1396, wherein said polypeptide is differentially expressed in cancer.

In some embodiments, the agent comprises an antibody or fragment thereof.

An isolated agent that selectively binds to an isolated polypeptide consisting of an amino acid sequence selected from the group consisting of SEQ ID NOs.: 9-33 or a fragment thereof, or an albumin protein fragment having a mass selected from the group consisting of about 2044, about 2098, about 2070, about 1013, about 1067, about 1639, about 999, about 1342, about 1396, about 1149, about 1405, about 1757, about 952, about 1169, about 1303, about 1623, about 1677, about 2403, about 2457, about 2413, about 2467, about 2541, about 2595, about 2559, about 2613, about 2720, about 2774, about 2916, about 2970, about 3362, about 3415 and about 1396, wherein said polypeptide is differentially expressed in cancer.

In some embodiments, the agent comprises an antibody or fragment thereof.

BRIEF DESCRIPTION OF THE DRAWINGS

FIG. 10 shows Mascot results including spectra of a polypeptide of mass about 1066 (SEQ ID NO:10).

FIG. 11 shows Mascot results including spectra of a polypeptide of mass about 1395 (SEQ ID NO:15).

FIG. 12 shows Mascot results including spectra of a polypeptide of mass about 2098 (SEQ ID NO:11).

FIG. 13 shows Mascot results including spectra of a polypeptide of mass about 2970 (SEQ ID NO:23).

DETAILED DESCRIPTION

Figure 1:
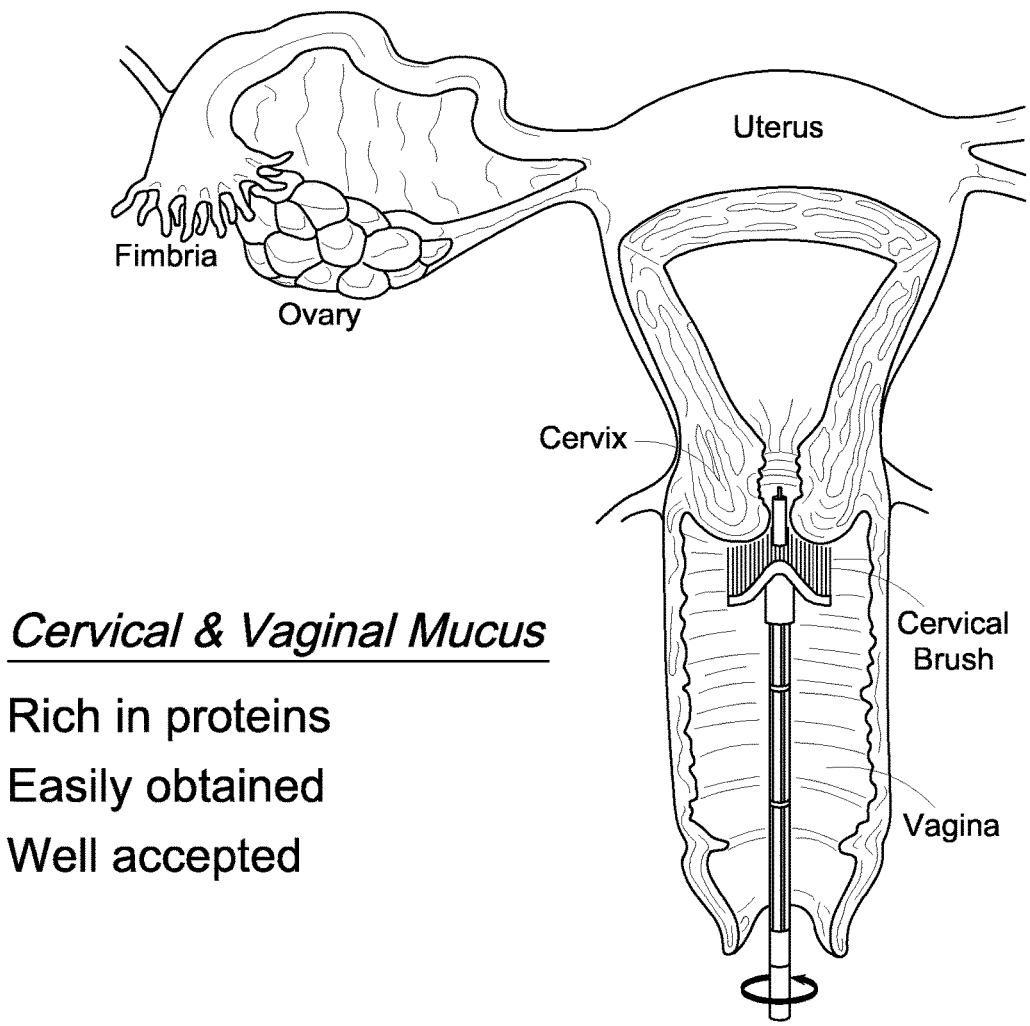
FIG. 1 is a diagram of an embodiment for use of a cervical brush to obtain a sample from the cervix of a subject.

Some embodiments of the present invention relate to methods and compositions for assessing the presence or absence of cancer. In particular, methods and compositions for detecting endometrial cancer or ovarian cancer are provided. Applicant has discovered that detection of certain target molecules in samples is indicative of the presence, absence, progression or stage of cancer. In particular embodiments, the cancer is endometrial cancer or ovarian cancer. Examples of the target molecules include certain polypeptides and fragments thereof, and nucleic acids encoding such polypeptides and fragments thereof. In some embodiments, the polypeptide comprises at least one residue associated with iron.

In some embodiments of the compositions and methods provided herein, the samples originate from the cervix, the vagina, or the posterior vaginal fornix of a subject.

Proteomic analysis of body fluids can yield information for biomarker discovery and treatment development. In some embodiments, the body fluids are cervico-vaginal fluids. Cervico-vaginal fluid samples are especially interesting in terms of gynecological diagnostics since these samples can easily be collected using non-invasive methods. Although conventional biomarkers are often quantified in plasma samples, there are two reasons why cervico-vaginal fluid samples are preferred over plasma samples in terms of gynecological biomarker discovery. First, since the volume of plasma (about 3 liters) is much larger than e.g. vaginal washings (about 50 ml), it could be expected that dilution of a (potential) biomarker will be much lower in the latter fluid. Second, altered biomarker expression patterns in plasma are often not very specific as they may be associated with different pathologies because plasma comes in contact with all organs of the body. In contrast, when using cervico-vaginal fluid samples, it is expected that expression patterns will directly correlate with gynecological pathologies.

In some embodiments, the present invention relates to methods for the identification of one or more iron modified polypeptides as well as iron modified polypeptides containing covalently bound iron present in a liquid solution derived from a female subject. In some embodiments, the liquid solution is generated as a by-product of a routine PAP test. In some embodiments, the test is generated by taking a sample from the cervix or vagina, and placing it in a liquid preservative solution and removing the cells and cellular debris from the liquid. In some embodiments, iron modified polypeptides can be differentially identified in samples from different individuals and that such iron modified polypeptides as well as iron modified polypeptides containing covalently bound iron may be used to differentiate subjects suffering from a disease and healthy subjects. In some embodiments, methods for generating an iron modified polypeptide profile are provided. In some embodiments, a profile includes iron modified polypeptides containing covalently bound iron from a subject. In some embodiments, methods of screening for and diagnosing various diseases are provided.

Biological Sample

A biological sample can include any body fluid or tissue. Preferred body fluids include blood, plasma, serum, urine, saliva, sputum, cerebrospinal fluid, mucus, and vaginal and rectal secretions. In some embodiments, the biological sample includes blood or blood products such as plasma and serum. Embodiments provided herein are directed toward the analysis of cancer, in particular, endometrial and ovarian cancers, tissues and fluids originating from the uterus, cervix, vagina and the like are preferred. When tissue samples are used, such as biopsies, they can be homogenized, for example in phosphate buffered saline or, alternatively, in a detergent-containing buffer to solubilize the polypeptides to be detected.

In some embodiments of the compositions and methods provided herein, a sample originates from the cervix, the vagina, or the posterior vaginal fornix of a subject. In some embodiments, the sample are obtained using methods described in U.S. application Ser. No. 12/646,592, entitled "NOVEL MOLECULAR ASSAY AND USES THEREOF", the disclosure of which is incorporated herein by reference in its entirety.

In some embodiments, samples are prepared by obtaining a sample of cervical cells and/or mucus from the cervix uteri and/or the posterior vaginal fornix by scraping and/or contacting the tissue with a device, such as, but not limited to, a spatula, a cotton swab, a cytobrush, sterile applicator or similar sampling device. Such devices may include devices made for the collection/absorption of gynecological discharges such as a tampon and the like. It is desirable for such devices to be free from endogenous polypeptides and other materials that could interfere with analyses. Mucus and/or cell released factors are also contained in this sampling. Suitable devices are described in U.S. Pat. No. 5,357,977 which is hereby incorporated by reference for such teachings.

In some embodiments, samples are obtained using an applicator having a tip portion for collection (such as 6" plastic shaft Dacron tipped applicator available from Solon Manufacturing, Inc.). The sample is obtained in accordance with good clinical practice in the medical community. In one embodiment, the sample is obtained by a health care professional, such as, but not limited to, a nurse, nurse practitioner or doctor. In an alternate embodiment, the sample is obtained by the subject. The sampling device containing the sample may then placed in a liquid solution. The sampling device may be incubated in the liquid solution for a predetermined amount of time, such as 5 seconds, 30 seconds, 1 minute or more or the sampling device may be left in the liquid solution to ensure the sample is removed from the sampling device and transferred to the liquid solution. The liquid solution may be vortexed or otherwise agitated when in contact with the sampling device to aid in this process.

In some embodiments, the sampling device is a tampon or similar device. Tampons are designed to collect gynecological fluids. During the insertion and/or removal, the tampon wipes the walls of the vaginal canal and samples the mucus discharge. Tampons may be left in for up to a maximum recommended time or placed in and removed almost immediately. In the present disclosure, residence times for the tampons range from 5 minutes to 4 hours. Analysis of the cell-released factors present was similar at all time points tested. Due to the possibility of contaminations from other discharges, a shorter time is preferred. The tampon may be placed into a sealed container and left at room temperature for an extended time with minimal loss of signal and polypeptide integrity. In one embodiment, the tampon is dropped into a preservative solution and stored in that until processing. The liquid solution is a preservative solution or contains a preservative that preserves the contents of the sample obtained.

In some embodiments, the liquid solution is a commercially available preservative solution. In some embodiments, the liquid solution is a commercially available preservative designed for use with samples containing proteins or polypeptides. In another embodiment, alternate liquid solutions may be used. Any liquid solution that is compatible with the cell released factor detection methodologies and that is compatible with the cell released factors may be used. In a particular embodiment, the liquid solution is a buffered water-based solution which comprises a preservative. In one embodiment, the preservative is one or more alcohols. Suitable alcohols include, but are not limited to, 1 to 10 carbon alcohols or mixtures thereof, such as methanol, ethanol, propanols, butanols, and pentanols. In a specific embodiment, the alcohol is ethanol. The preservative can comprise from about 1% to about 75% of the liquid solution. The liquid solution may optionally contain a buffering agent. The buffering agent is selected to maintain the pH of the liquid solution at any pH desired by the user. In one embodiment, the buffering agent is selected to maintain the liquid solution in a pH range of about 2.5 to about 9 or from about 3 to about 8. Any buffering agent that has buffering capacity in the indicated pH ranges can be used in the, such as, but not limited to, glycine, maleic, phosphoric, tartaric, citric, formic, or acetic acids and the like. The buffering can comprise from about 1% to about 50% of the preservative solution. The liquid solution may also contain additional components such as one or more fixatives, anti-microbial agents and/or protease inhibitors. The fixative may be present from about 1% to about 15% of the preservative solution. Exemplary fixatives include, but are not limited to, aldehydes such formaldehyde, glutaraldehyde and the like, polypropylene glycol, polyethylene glycol, EDTA, or any combination of the foregoing. Exemplary anti-microbial agents include, but are not limited to, aminoglycosides, tJ-lactams, polymixins cephalosporins, quinolones, sulfonamides, tetracyclines, macrolides, penicillins, azides, organic acids and essential oils; other anti-microbial compounds currently known or discovered hereafter may also be used. Exemplary protease inhibitors include, but are not limited to chelating agents (such as, but not limited to, murexide, chromotropic acid, 1-(I-hydroxy-2-napththylazo-2-hydroxy-5-nitronaphthalene-4-sulphonic acid, EGTA (ethylene glycol tetraacetic acid), EDTA (ethylenediaminetetraacetic acid), o-phenanthroline, and thiourea), leupeptin, pepstatin A, aprotinin, phenylmethylsulfonylfluorde, hirudin, trypsin inhibitor and trypsin-chymotrypsin inhibitor; other protease inhibitors currently known or discovered hereafter may also be used. The liquid solution is retained for further analysis as described herein. The liquid solution may be stored at room/ambient temperature or may be stored at 4° C. or colder (for example, −80° C. or in liquid nitrogen). In some embodiments, the preservative solution acts as a preservative of the polypeptides contained in the liquid solution. The liquid solution may be analyzed immediately or stored for future analysis. In one embodiment, storage is at ambient temperature; in an alternate embodiment, storage is at 4° C.; in a further alternate embodiment, storage is at −20° C.; in a yet another embodiment, storage is at −80° C. until analysis.

In one embodiment of the disclosure, the liquid solution is obtained as a by-product of a liquid-based PAP test. It should be noted that any liquid based PAP test may be used in conjunction with the present disclosure. The PAP test kits are used according to the manufacturer's instructions and good clinical practice. For example, a commercially available PAP test sample may be obtained by either the combination cytobrush/plastic spatula sampling device (such as from Medscand USA, Hollywood, Fla.) or the broom-type sampling device (such as from; Wallach Surgical Devices, Millford, Conn.). The collected material is rinsed directly into a liquid based preservative solution. The liquid solution resulting from the PAP test procedure is generally stored but is not used for diagnostic or other applications. In some embodiments, the liquid solution is obtained through swabbing and/or contacting the posterior vaginal fornix or the vaginal canal with a cotton swab, gauze, sterile applicator or similar sampling device. In one embodiment, the sampling device is a 6" plastic shaft Dacron-tipped sterile applicator (available from Solon Manufacturing, Inc.).

Sample Processing

In some embodiments, a test sample can be preprocessed prior to analysis of its protein content, for example to remove nonproteinaceous sample components. Methods for preprocessing include, without limitation, various forms of chromatography (size exclusion, hydrophobic, ion exchange, affinity and the like), microfiltration, centrifugation and dialysis. Preprocessing also can include subjecting the sample to chemical or enzymatic protein cleavage agents in order to break down the proteins into smaller components. Additionally or alternatively, the test sample is optionally fractionated into subsamples, each containing a subset of sample proteins, prior to analyzing the sample for polypeptide biomarkers. In some embodiments, the sample can be pre-processed to remove substantially al of the cells.

The amount of a target molecule, such as a polypeptide or fragment thereof, in the test sample or a control sample can be zero, in which case "amount" refers to the presence or absence of the target molecule, which presence or absence is indicative of a cancer. Alternatively, the target molecule can be present in both samples, but at a higher (upregulated) or lower (downregulated) level in the test sample which is indicative of cancer.

Amounts of target molecules can be determined in absolute or relative terms. If expressed in relative terms, amounts can be expressed as normalized amounts with reference to a selected target molecule present in the sample.

In some embodiments, after optional preprocessing and/or fractionation, target molecules are physically separated prior to determining the amounts of each target molecules. Physical separation can be achieved, for example, using single or multidimensional chromatography, electrochromatography or electrophoresis, such as 2D electrophoresis. The amount of the separated target molecules can be determined using any convenient method such as spectroscopic (e.g., UV detection) or colorimetric (e.g., staining) methods. Optionally, the identity of separated target molecules of interest can be determined using standard techniques such as protein sequencing and tandem mass spectrometry.

In other embodiments of the invention, after optional preprocessing and/or fractionation, sample components are not further separated but instead the sample is subjected to mass analysis, for example using peptide-mass fingerprinting or mass spectrometry.

Methods for Detecting Target Molecules

Target molecules can be detected by any means known in the art. By way of non-limiting example, polypeptide target molecules may be detected by using immunohistological, immunocytological, hybridization using immunofluorescence and/or immunoenzymatic, techniques as well as hydrometry, polarimetry, spectrophotometry (e.g., mass and NMR) and chromatography (e.g., gas liquid, high performance liquid, and thin layer). In some embodiments, nucleic acid target molecules may be detected using nucleic acid hybridization methods, such as Southern blotting, Northern blotting, or PCR.

Some embodiments of the methods and compositions provided herein include characterizing a target molecule in a sample, such as a sample obtained from the cervix, the vagina, or the posterior vaginal fornix. Characterizing a target molecule can include, for example, identifying a target molecule, detecting a target molecule, and/or quantifying a target molecule. Methods to identify, detect and quantify target molecule are well known in the art.

Some embodiments include identifying, determining the presence or absence of a target molecule, and/or quantifying a target molecule, wherein the target molecule comprises a peptide, polypeptide, and/or protein.

As used in the present specification, the term "polypeptide" and "protein", used interchangeably herein, refer to a polymer of amino acids without regard to the length of the polymer; thus, peptides, oligopeptides, and proteins are included within the definition of polypeptide. This term also includes wild-type polypeptides, as well as mutants, truncations, extensions, splice-variants, and other non-native forms of polypeptide that may be present. This term also includes forms of the foregoing that have been subject to enzymatic degradation by proteases or other mechanisms (enzymatic or non-enzymatic) in the subject. For example, a polypeptide may be subject to degradation by a protease to produce a polypeptide fragment of the polypeptide. The protease may be one that is expressed or increased in expression as a result of the health problem or disease of the gynecological system. Alternatively, the protease may be added to the sample to digest the polypeptides therein into fragments. In some embodiments, trypsin may be added to the sample. The polypeptide may have been originally on a cellular surface but proteolytically processed or removed as a result of a disease process and collected into the mucus. This term also does not specify or exclude chemical or post-expression/translational modifications of the polypeptides, although chemical or post-expression modifications of these polypeptides may be included or excluded as specific embodiments. Therefore, for example, modifications to polypeptides that include the covalent attachment of glycosyl groups (i.e., glycosylation), acetyl groups (i.e., acetylation), phosphate groups (phosphorylation, including, but not limited to, phosphorylation on serine, threonine and tyrosine groups), lipid groups and the like are expressly encompassed by the term polypeptide. Further, polypeptides with these modifications may be specified as individual species to be included or excluded. The natural or other chemical modifications, such as those listed in examples above can occur anywhere in a polypeptide, including the peptide backbone, the amino acid side-chains and the amino or carboxyl termini, and may be present in the same or varying degrees at several sites in a given polypeptide. Also, a given polypeptide may contain many types of modifications. Polypeptides may be branched, for example, as a result of ubiquitination, and they may be cyclic, with or without branching. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formylation of cysteine, formylation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination (see, for instance Creighton, (1993), Posttranslational Covalent Modification of Proteins, W. H. Freeman and Company, New York B. C. Johnson, Ed., Academic Press, New York 1-12; Seifier, et al., (1990) Meth Enzymol 182:626-646; Rattan et al, (1992) Ann NY Acad Sci 663:48-62). In some embodiments, at least one residue of a polypeptide is associated with iron.

Such target polypeptide molecules may be characterized by a variety of methods such as immunoassays, including radioimmunoassays, enzyme-linked immunoassays and two-antibody sandwich assays as described herein. A variety of immunoassay formats, including competitive and non-competitive immunoassay formats, antigen capture assays and two-antibody sandwich assays also are useful (Self and Cook, (1996) Curr. Opin. Biotechnol. 7:60-65, incorporated by reference in its entirety). Some embodiments include one or more antigen capture assays. In an antigen capture assay, antibody is bound to a solid phase, and sample is added such that antigen, e.g., a target molecule in a fluid or tissue sample, is bound by the antibody. After unbound proteins are removed by washing, the amount of bound antigen can be quantitated, if desired, using, for example, a radioassay (Harlow and Lane, (1988) Antibodies A Laboratory Manual Cold Spring Harbor Laboratory: New York, incorporated by reference in its entirety), or a colorimetric assay. Immunoassays can be performed under conditions of antibody excess, or as antigen competitions, to quantitate the amount of antigen and, thus, determine a level of a target molecule in a sample, such as a sample obtained from the cervix, the vagina, or the posterior vaginal fornix.

Enzyme-linked immunosorbent assays (ELISAs) can be useful in certain embodiments provided herein. An enzyme such as horseradish peroxidase (HRP), alkaline phosphatase (AP), β-galactosidase or urease can be linked, for example, to an anti-HMGB1 antibody or to a secondary antibody for use in a method of the invention. A horseradish-peroxidase detection system can be used, for example, with the chromogenic substrate tetramethylbenzidine (TMB), which yields a soluble product in the presence of hydrogen peroxide that is detectable at 450 nm. Other convenient enzyme-linked systems include, for example, the alkaline phosphatase detection system, which can be used with the chromogenic substrate p-nitrophenyl phosphate to yield a soluble product readily detectable at 405 nm. Similarly, a β-galactosidase detection system can be used with the chromogenic substrate o-nitrophenyl-β-D-galactopyranoside (ONPG) to yield a soluble product detectable at 410 nm, or a urease detection system can be used with a substrate such as urea-bromocresol purple (Sigma Immunochemicals). Useful enzyme-linked primary and secondary antibodies can be obtained from a number of commercial sources such as Jackson Immuno-Research (West Grove, Pa.) as described further herein.

In certain embodiments, a target molecule in a sample, such as a sample obtained from the cervix, the vagina, or the posterior vaginal fornix, can be detected and/or measured using chemiluminescent detection. For example in certain embodiments, specific antibodies to a particular target molecule are used to capture the target molecule present in the biological sample, e.g., such as a sample obtained from the cervix, the vagina, or the posterior vaginal fornix, and an antibody specific for the target molecule-specific antibodies and labeled with an chemiluminescent label is used to detect the target molecule present in the sample. Any chemiluminescent label and detection system can be used in the present methods. Chemiluminescent secondary antibodies can be obtained commercially from various sources such as Amersham. Methods of detecting chemiluminescent secondary antibodies are known in the art.

Fluorescent detection also can be useful for detecting a target molecule in certain methods provided herein. Useful fluorochromes include, DAPI, fluorescein, Hoechst 33258, R-phycocyanin, B-phycoerythrin, R-phycoerythrin, rhodamine, Texas red and lissamine. Fluorescein or rhodamine labeled antibodies, or fluorescein- or rhodamine-labeled secondary antibodies can be useful in the invention.

Radioimmunoassays (RIAs) also can be useful in certain methods provided herein. Such assays are well known in the art. Radioimmunoassays can be performed, for example, with $^{125}$I-labeled primary or secondary antibody (Harlow and Lane, (1988) Antibodies A Laboratory Manual Cold Spring Harbor Laboratory: New York, incorporated by reference in its entirety).

A signal from a detectable reagent can be analyzed, for example, using a spectrophotometer to detect color from a chromogenic substrate; a radiation counter to detect radiation, such as a gamma counter for detection of $^{125}$I; or a fluorometer to detect fluorescence in the presence of light of a certain wavelength. Where an enzyme-linked assay is used, quantitative analysis of the amount of a target molecule can be performed using a spectrophotometer such as an EMAX Microplate Reader (Molecular Devices; Menlo Park, Calif.) in accordance with the manufacturer's instructions. The assays of the invention can be automated or performed robotically, if desired, and that the signal from multiple samples can be detected simultaneously.

In some embodiments, capillary electrophoresis based immunoassays (CEIA), which can be automated if desired, may be used to detect and/or measure the target molecule. Immunoassays also can be used in conjunction with laser-induced fluorescence as described, for example, in Schmalzing and Nashabeh, Electrophoresis 18:2184-93 (1997), and Bao, J. Chromatogr. B. Biomed. Sci. 699:463-80 (1997), each incorporated by reference in its entirety. Liposome immunoassays, such as flow-injection liposome immunoassays and liposome immunosensors, also can be used to detect target molecules or to determine a level of a target molecule according to certain methods provided herein (Rongen et al., (1997) J. Immunol. Methods 204:105-133, incorporated by reference in its entirety).

Sandwich enzyme immunoassays also can be useful in certain embodiments. In a two-antibody sandwich assay, a first antibody is bound to a solid support, and the antigen is allowed to bind to the first antibody. The amount of a target molecule is quantitated by measuring the amount of a second antibody that binds to it.

In an example sandwich assay, an agent that selectively binds to a target molecule can be immobilized on a solid support. A capture reagent can be chosen to directly bind the target molecule or indirectly bind the target molecule by binding with an ancillary specific binding member which is bound to the target molecule. In addition, the capture reagent may be immobilized on the solid phase before or during the performance of the assay by means of any suitable attachment method. Typically, the capture site of the present invention is a delimited or defined portion of the solid phase such that the specific binding reaction of the capture reagent and analyte is localized or concentrated in a limited site, thereby facilitating the detection of label that is immobilized at the capture site in contrast to other portions of the solid phase. In a related embodiment, the capture reagent can be applied to the solid phase by dipping, inscribing with a pen, dispensing through a capillary tube, or through the use of reagent jet-printing or other techniques. In addition, the capture zone can be marked, for example with a dye, such that the position of the capture zone upon the solid phase can be visually or instrumentally determined even when there is no label immobilized at the site.

Another example embodiment of a sandwich assay format includes methods and compositions wherein a sample is mixed with a labeled first specific binding pair member for the target molecule and allowed to traverse a lateral flow matrix, past a series of spatially separated capture zones located on the matrix (See e.g., U.S. Pat. No. 7,491,551, incorporated by reference in its entirety). The sample may be mixed with the labeled first specific binding pair member prior to addition of the sample to the matrix. Alternatively, the labeled first specific binding pair member may be diffusively bound on the matrix on a labeling zone at a point upstream of the series of capture zones. Sometimes, the sample is added directly to the labeling zone. Preferably, the sample is added to a sample receiving zone on the matrix at a point upstream of the labeling zone and allowed to flow through the labeling zone. The labeled first specific binding pair member located within the labeling zone is capable of being freely suspendable in the sample. Therefore, if analyte is present in the sample, the labeled first specific binding pair member will bind to the target molecule and the resulting target molecule-labeled first specific binding pair member complex will be transported to and through the capture zones. The extent of complex formation between the target molecule and the labeled specific binding pair member is, directly proportional to the amount of target molecule present in the sample. A second specific binding pair member capable of binding to the target molecule-first specific binding pair member complex is immobilized on each of the capture zones. This second specific binding pair member is not capable of binding the labeled specific binding pair member unless the labeled specific binding pair member is bound to the target molecule. Thus, the amount of labeled specific binding pair member that accumulates on the capture zones is directly proportional to the amount of target molecule present in the sample.

In some embodiments, an assay includes the use of binding agent immobilized on a solid support to bind to and remove a target polypeptide from the remainder of the sample. The bound target polypeptide may then be detected using a detection reagent that contains a reporter group and specifically binds to the binding agent/polypeptide complex. Such detection reagents may comprise, for example, a binding agent that specifically binds to the target polypeptide or an antibody or other agent that specifically binds to the binding agent, such as an anti-immunoglobulin, protein G, protein A or a lectin. In such embodiments, the binding agent can comprise an antibody or fragment thereof specific to a polypeptide or fragment thereof described herein. Alternatively, a competitive assay may be utilized, in which a polypeptide is labeled with a reporter group and allowed to bind to the immobilized binding agent after incubation of the binding agent with the sample. The extent to which components of the sample inhibit the binding of the labeled polypeptide to the binding agent is indicative of the reactivity of the sample with the immobilized binding agent. Suitable polypeptides for use within such assays include full length proteins provided herein and polypeptide portions thereof such as SEQ ID NOs:9-33, and an albumin protein fragment having a mass selected from the group consisting of about 2044, about 2098, about 2070, about 1013, about 1067, about 1639, about 999, about 1342, about 1396, about 1149, about 1405, about 1757, about 952, about 1169, about 1303, about 1623, about 1677, about 2403, about 2457, about 2413, about 2467, about 2541, about 2595, about 2559, about 2613, about 2720, about 2774, about 2916, about 2970, about 3362, about 3415 and about 1396, to which the binding agent binds. An example for a human albumin protein is provided in SEQ ID NO:22.

The solid support may be any material known to those of ordinary skill in the art to which the binding agent may be attached. For example, the solid support may be a test well in a microtiter plate or a nitrocellulose or other suitable membrane, or a flow-through format, or a test strip. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the agent and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of binding agent ranging from about 10 ng to about 10 µg, and preferably about 100 ng to about 1 µg, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12-A13).

In certain embodiments, the assay is a two-antibody sandwich assay. This assay may be performed by first contacting an antibody that has been immobilized on a solid support, commonly the well of a microtiter plate, with the sample, such that target polypeptides within the sample are allowed to bind to the immobilized antibody. Unbound sample is then removed from the immobilized polypeptide-antibody complexes and a detection reagent (preferably a second antibody capable of binding to a different site on the polypeptide) containing a reporter group is added. The amount of detection reagent that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art may be used, such as bovine serum albumin or TWEEN 20. (Sigma Chemical Co., St. Louis, Mo.). The immobilized antibody is then incubated with the sample, and target polypeptide is allowed to bind to the antibody. The sample may be diluted with a suitable diluent, such as phosphate-buffered saline (PBS) prior to incubation. In general, an appropriate contact time (i.e., incubation time) is a period of time that is sufficient to detect the presence of target polypeptide within a sample obtained from an individual. Preferably, the contact time is sufficient to achieve a level of binding that is at least about 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% TWEEN 20. The second antibody, which contains a reporter group, may then be added to the solid support. Reporter groups are well known in the art. The detection reagent is then incubated with the immobilized antibody-polypeptide complex for an amount of time sufficient to detect the bound detection reagent. An appropriate amount of time may generally be determined by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the level of a marker such as a polypeptide described herein e.g., SEQ ID NO:9-33 or an albumin protein fragment having a mass selected from the group consisting of about 2044, about 2098, about 2070, about 1013, about 1067, about 1639, about 999, about 1342, about 1396, about 1149, about 1405, about 1757, about 952, about 1169, about 1303, about 1623, about 1677, about 2403, about 2457, about 2413, about 2467, about 2541, about 2595, about 2559, about 2613, about 2720, about 2774, about 2916, about 2970, about 3362, about 3415 and about 1396, the signal detected from the reporter group that remains bound to the solid support may be compared to a signal that corresponds to a predetermined cut-off value. In one embodiment, the cut-off value for the detection of a cancer is the average mean signal obtained when the immobilized antibody is incubated with samples from patients without the cancer. In general, a sample generating a signal that is three standard deviations above or below the predetermined cut-off value is considered positive for the cancer. For example, an increased level of certain polypeptides described herein e.g., SEQ ID NO:9-33 or an albumin protein fragment having a mass selected from the group consisting of about 2044, about 2098, about 2070, about 1013, about 1067, about 1639, about 999, about 1342, about 1396, about 1149, about 1405, about 1757, about 952, about 1169, about 1303, about 1623, about 1677, about 2403, about 2457, about 2413, about 2467, about 2541, about 2595, about 2559, about 2613, about 2720, about 2774, about 2916, about 2970, about 3362, about 3415 and about 1396, may be indicative of the presence of cancer or the stage of cancer. Similarly, a reduced level of certain polypeptides described herein may be indicative of the presence of cancer or the stage of cancer. In some embodiments, the cut-off value is determined using a Receiver Operator Curve, according to the method of Sackett et al., Clinical Epidemiology: A Basic Science for Clinical Medicine, Little Brown and Co., 1985, p. 106-7. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate.

In a related embodiment, the assay is performed in a flow-through or test strip format, wherein the binding agent is immobilized on a membrane, such as nitrocellulose. In the flow-through test, target polypeptides within the sample bind to the immobilized binding agent as the sample passes through the membrane. A second, labeled binding agent then binds to the binding agent-polypeptide complex as a solution containing the second binding agent flows through the membrane. The detection of bound second binding agent may then be performed as described herein. In the strip test format, one end of the membrane to which binding agent is bound is immersed in a solution containing the sample. The sample migrates along the membrane through a region containing second binding agent and to the area of immobilized binding agent. The amount of immobilized antibody indicates the presence, or absence or progression or stage of a cancer. Typically, the concentration of second binding agent at that site generates a pattern, such as a line, that can be read visually. In general, the amount of binding agent immobilized on the membrane is selected to generate a visually discernible pattern when the biological sample contains a level of polypeptide that would be sufficient to generate a positive signal in the two-antibody sandwich assay, in the format discussed above. Preferred binding agents for use in such assays are antibodies and antigen-binding fragments thereof. Preferably, the amount of antibody immobilized on the membrane ranges from about 25 ng to about 1 μg, and more preferably from about 50 ng to about 500 ng. Such tests can typically be performed with a very small amount of biological sample.

Quantitative Western blotting also can be used to detect a target molecule or to determine a level of target molecule in a method provided herein. Western blots can be quantitated by well known methods such as scanning densitometry. As an example, protein samples are electrophoresed on 10% SDS-PAGE Laemmli gels. Primary murine monoclonal antibodies, for example, against a target molecule are reacted with the blot, and antibody binding confirmed to be linear using a preliminary slot blot experiment. Goat anti-mouse horseradish peroxidase-coupled antibodies (BioRad) are used as the secondary antibody, and signal detection performed using chemiluminescence, for example, with the Renaissance chemiluminescence kit (New England Nuclear; Boston, Mass.) according to the manufacturer's instructions. Autoradiographs of the blots are analyzed using a scanning densitometer (Molecular Dynamics; Sunnyvale, Calif.) and normalized to a positive control. Values are reported, for example, as a ratio between the actual value to the positive control (densitometric index). Such methods are well known in the art as described, for example, in Parra et al., J. Vasc. Surg. 28:669-675 (1998), incorporated herein by reference in its entirety.

As described herein, immunoassays including, for example, enzyme-linked immunosorbent assays, radioimmunoassays and quantitative western analysis, can be useful in some embodiments for detecting a target molecule or determining a level of a target molecule. Such assays typically rely on one or more antibodies. As would be understood by the skilled artisan, methods described herein can be used to readily distinguish proteins with alternative forms of post-translation modifications, e.g., phosphorylated proteins, and glycosylated proteins.

Some embodiments of the methods and compositions provided herein include generating agents that selectively bind to target molecules. In some embodiments, such agents include an antibody or fragment thereof. Methods of generating polyclonal antibodies and monoclonal antibodies are well known in the art. The antibodies or active fragments thereof may be obtained by methods known in the art for production of antibodies or functional portions thereof. Such methods include, but are not limited to, separating B cells with cell-surface antibodies of the desired specificity, cloning the DNA expressing the variable regions of the light and heavy chains and expressing the recombinant genes in a suitable host cell. Standard monoclonal antibody generation techniques can be used wherein the antibodies are obtained from immortalized antibody-producing hybridoma cells. These hybridomas can be produced by immunizing animals with HSCs or progeny thereof, and fusing B lymphocytes from the immunized animals, preferably isolated from the immunized host spleen, with compatible immortalized cells, preferably a B cell myeloma.

Target molecules, such as protein target molecules, can be characterized by a variety of methods. Proteins, polypeptides and peptides can be isolated by a variety of methods well known in the art, such as protein precipitation, chromatography (e.g., reverse phase chromatography, size exclusion chromatography, ion exchange chromatography, liquid chromatography), affinity capture, and differential extractions.

Isolated proteins can under go enzymatic digestion or chemical cleavage to yield polypeptide fragments and peptides. Such fragments can be identified and quantified. A particularly useful method for analysis of polypeptide/peptide fragments and other target molecules is mass spectrometry (U.S. Pat. App. No. 20100279382, incorporated by reference in its entirety). A number of mass spectrometry-based quantitative proteomics methods have been developed that identify the proteins contained in each sample and determine the relative abundance of each identified protein across samples (Flory et al., Trends Biotechnol. 20:523-29 (2002); Aebersold, J. Am. Soc. Mass Spectrom. 14:685-695

(2003); Aebersold, J. Infect. Dis. 187 Suppl 2:S315-320 (2003); Patterson and Aebersold, Nat. Genet. 33 Suppl, 311-323 (2003); Aebersold and Mann, Nature 422:198-207 (2003); Aebersold, R. and Cravatt, Trends Biotechnol. 20:S1-2 (2002); Aebersold and Goodlett, Chem. Rev. 101, 269-295 (2001); Tao and Aebersold, Curr. Opin. Biotechnol. 14:110-118 (2003), each incorporated by reference in its entirety). Generally, the proteins in each sample are labeled to acquire an isotopic signature that identifies their sample of origin and provides the basis for accurate mass spectrometric quantification. Samples with different isotopic signatures are then combined and analyzed, typically by multidimensional chromatography tandem mass spectrometry. The resulting collision induced dissociation (CID) spectra are then assigned to peptide sequences and the relative abundance of each detected protein in each sample is calculated based on the relative signal intensities for the differentially isotopically labeled peptides of identical sequence.

More techniques for identifying and quantifying target molecules include label-free quantitative proteomics methods. Such methods include: (i) sample preparation including protein extraction, reduction, alkylation, and digestion; (ii) sample separation by liquid chromatography (LC or LC/LC) and analysis by MS/MS; (iii) data analysis including peptide/protein identification, quantification, and statistical analysis. Each sample can be separately prepared, then subjected to individual LC-MS/MS or LC/LC-MS/MS runs (Zhu W. et al., J. of Biomedicine and Biotech. (2010) Article ID 840518, 6 pages, incorporated by reference in its entirety). An example technique includes LC-MS in which the mass of a peptide coupled with its corresponding chromatographic elution time as peptide properties that uniquely define a peptide sequence, a method termed the accurate mass and time (AMT) tag approach. Using LC coupled with Fourier transform ion cyclotron resonance (LC-FTICR) MS to obtain the chromatographic and high mass accuracy information, peptide sequences can be identified by matching the AMT tags to previously acquired LC-MS/MS sequence information stored in a database. By taking advantage of the observed linear correlation between peak area of measured peptides and their abundance, these peptides can be relatively quantified by the signal intensity ratio of their corresponding peaks compared between MS runs (Tang, K., et al., (2004) J. Am. Soc. Mass Spectrom. 15:1416-1423; and Chelius, D. and Bondarenko, P. V. (2002) J. Proteome Res. 1: 317-323, incorporated by reference in their entireties). Statistics tools such as the Student's t-test can be used to analyse data from multiple LC-MS runs for each sample (Wiener, M. C., et al., (2004) Anal. Chem. 76:6085-6096, incorporated by reference in its entirety). At each point of acquisition time and m/z, the amplitudes of signal intensities from multiple LC-MS runs can be compared between two samples to detect peptides with statistically significant differences in abundance between samples.

As will be understood, a variety of mass spectrometry systems can be employed in the methods for identifying and/or quantifying a polypeptide/peptide fragments. Mass analyzers with high mass accuracy, high sensitivity and high resolution include, ion trap, triple quadrupole, and time-of-flight, quadrupole time-of-flight mass spectrometeres and Fourier transform ion cyclotron mass analyzers (FT-ICR-MS). Mass spectrometers are typically equipped with matrix-assisted laser desorption (MALDI) or electrospray ionization (ESI) ion sources, although other methods of peptide ionization can also be used. In ion trap MS, analytes are ionized by ESI or MALDI and then put into an ion trap. Trapped ions can then be separately analyzed by MS upon selective release from the ion trap. Fragments can also be generated in the ion trap and analyzed. Sample molecules such as released polypeptide/peptide fragments can be analyzed, for example, by single stage mass spectrometry with a MALDI-TOF or ESI-TOF system. Methods of mass spectrometry analysis are well known to those skilled in the art (see, e.g., Yates, J. (1998) Mass Spect. 33:1-19; Kinter and Sherman, (2000) Protein Sequencing and Identification Using Tandem Mass. Spectrometry, John Wiley & Sons, New York; and Aebersold and Goodlett, (2001) Chem. Rev. 101:269-295, each incorporated by reference in its entirety).

For high resolution polypeptide fragment separation, liquid chromatography ESI-MS/MS or automated LC-MS/MS, which utilizes capillary reverse phase chromatography as the separation method, can be used (Yates et al., Methods Mol. Biol. 112:553-569 (1999), incorporated by reference in its entirety). Data dependent collision-induced dissociation (CID) with dynamic exclusion can also be used as the mass spectrometric method (Goodlett, et al., Anal. Chem. 72:1112-1118 (2000), incorporated by reference in its entirety).

Once a peptide is analyzed by MS/MS, the resulting CID spectrum can be compared to databases for the determination of the identity of the isolated peptide. Methods for protein identification using single peptides have been described previously (Aebersold and Goodlett, Chem. Rev. 101:269-295 (2001); Yates, J. Mass Spec. 33:1-19 (1998), David N. et al., Electrophoresis, 20 3551-67 (1999), each incorporated by reference in its entirety). In particular, it is possible that one or a few peptide fragments can be used to identify a parent polypeptide from which the fragments were derived if the peptides provide a unique signature for the parent polypeptide. Moreover, identification of a single peptide, alone or in combination with knowledge of a site of glycosylation, can be used to identify a parent glycopolypeptide from which the glycopeptide fragments were derived. As will be understood, methods that include MS can be used to characterize proteins, fragments thereof, as well as other types of target molecules described herein.

In some embodiments, target molecules include nucleic acids. Nucleic acids can encode a polypeptide or fragment thereof useful to determine the presence or absence of a cancer. As such, target molecules include nucleic acid molecules sufficient for use as hybridization probes to identify nucleic acid molecules that correspond to a target molecule, including nucleic acids which encode a polypeptide corresponding to a target molecules, and fragments of such nucleic acid molecules, e.g., those suitable for use as PCR primers for the amplification or mutation of nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

A nucleic acid target molecule can be amplified using cDNA, mRNA, or genomic DNA as a template and appropriate oligonucleotide primers according to standard PCR amplification techniques. The nucleic acid so amplified can be cloned into an appropriate vector and characterized by DNA sequence analysis. Furthermore, oligonucleotides corresponding to all or a portion of a nucleic acid target molecule can be prepared by standard synthetic techniques, e.g., using an automated DNA synthesizer.

In another preferred embodiment, a nucleic acid target molecule comprises a nucleic acid molecule that has a nucleotide sequence complementary to a nucleic acid which is differentially expressed in cancer or a fragment thereof. For example, the target molecule may comprise a nucleic acid encoding a polypeptide of any one of SEQ ID NOs.: 9-33 or a fragment comprising at least 10, at least 20, at least 30, at least 40, at least 50 or more consecutive nucleotides thereof. A nucleic acid molecule which is complementary to a given nucleotide sequence is one which is sufficiently complementary to the given nucleotide sequence that it can hybridize to the given nucleotide sequence thereby forming a stable duplex.

Moreover, a nucleic acid target molecule can comprise all or only a portion of a nucleic acid sequence which is differentially expressed in cancer. For example, the target molecule may comprise a nucleic acid encoding a polypeptide of SEQ ID NOs.:9-33, a nucleic acid encoding a fragment of a polypeptide of SEQ ID NOs.:9-33, or a nucleic acid encoding an albumin protein fragment having a mass selected from the group consisting of about 2044, about 2098, about 2070, about 1013, about 1067, about 1639, about 999, about 1342, about 1396, about 1149, about 1405, about 1757, about 952, about 1169, about 1303, about 1623, about 1677, about 2403, about 2457, about 2413, about 2467, about 2541, about 2595, about 2559, about 2613, about 2720, about 2774, about 2916, about 2970, about 3362, about 3415 and about 1396, or a fragment comprising at least 10, at least 20, at least 30, at least 40, at least 50 or more consecutive nucleotides thereof. Such nucleic acids can be used, for example, as a probe or primer. The probe/primer typically is used as one or more substantially purified oligonucleotides. The oligonucleotide typically comprises a region of nucleotide sequence that hybridizes under stringent conditions to at least about 7, preferably about 15, more preferably about 25, 50, 75, 100, 125, 150, 175, 200, 250, 300, 350, or 400 or more consecutive nucleotides of a nucleic acid.

In some embodiments provided herein, a fragment of a polynucleotide sequence will be understood to include any nucleotide fragment having, for example, at least about 5 successive nucleotides, at least about 12 successive nucleotides, at least about 15 successive nucleotides, at least about 18 successive nucleotides, or at least about 20 successive nucleotides of the sequence from which it is derived. An upper limit for a fragment can include, for example, the total number of nucleotides in a full-length sequence encoding a particular polypeptide. A fragment of a polypeptide sequence will be understood to include any polypeptide fragment having, for example, at least about 5 successive residues, at least about 12 successive residues, at least about 15 successive residues, at least about 18 successive residues, or at least about 20 successive residues of the sequence from which it is derived. An upper limit for a fragment can include, for example, one less than the total number of residues in a full-length sequence of a particular polypeptide. Thus, a fragment may include, for example, a portion of a polypeptide comprising between at least 5 consecutive amino acids, and one less than the number of amino acids in the full length sequence of a particular polypeptide.

Probes based on the sequence of a nucleic acid target molecule can be used to detect transcripts or genomic sequences corresponding to one or more target molecules. The probe comprises a label group attached thereto, e.g., a radioisotope, a fluorescent compound, an enzyme, or an enzyme co-factor. Such probes can be used as part of a diagnostic test kit for identifying a biological sample, such as fluids, cells or tissues, which mis-express the protein, such as by measuring levels of a nucleic acid molecule encoding the protein in a sample of a fluid or cells from a subject, e.g., detecting mRNA levels or determining whether a gene encoding the protein has been mutated or deleted. Embodiments also include nucleic acid target molecules that differ, due to degeneracy of the genetic code, from the nucleotide sequence of nucleic acids encoding a protein that corresponds to a target molecule, and thus encode the same protein.

Method for Assessing the Presence, Absence, Progression or Stage of a Cancer

Some of the methods and composition provided herein include methods for assessing the presence of a cancer in a female subject. Some such embodiments include determining the level of at least one target molecule in a sample from said subject. In some embodiments, the target molecule comprises at least one polypeptide or fragment thereof or at least one nucleic acid encoding the polypeptide. In some embodiments, the polypeptide or fragment thereof comprises, consists essentially of, or consists of an amino acid sequence selected from SEQ ID NOs.:9-33. In some embodiments, the polypeptide or fragment thereof comprises, consists essentially of, consists of an albumin protein fragment having a mass selected from the group consisting of about 2044, about 2098, about 2070, about 1013, about 1067, about 1639, about 999, about 1342, about 1396, about 1149, about 1405, about 1757, about 952, about 1169, about 1303, about 1623, about 1677, about 2403, about 2457, about 2413, about 2467, about 2541, about 2595, about 2559, about 2613, about 2720, about 2774, about 2916, about 2970, about 3362, about 3415 and about 1396. In some embodiments, the mass of the polypeptides may be determined using mass spectrometry, such as the methodology described in Example 2. In some embodiments, the polypeptide comprises at least one residue associated with iron.

As used herein, "consisting essentially of" refers to a peptide or polypeptide which includes an amino acid sequence of the polypeptides provided herein, for example, SEQ ID NOs.: 9-33, along with additional amino acids at the carboxyl and/or amino terminal ends. For example, in some embodiments a polypeptide includes an amino acid sequence of the polypeptides provided herein, for example, SEQ ID NOs.: 9-33, along with no more than 1, no more than 2, no more than 3, no more than 4, no more than 5, no more than 6, no more than 7, no more than 8, no more than 9, or no more than 10 additional amino acid(s) at the carboxyl and/or amino terminal ends of a polypeptide provided herein, for example, one of SEQ ID NOs.: 9-33.

In some embodiments, the sample is obtained from the gynecological tract of a subject. The gynecological tract of a subject can include the ovary, oviduct, endometrium, cervix, vagina, and posterior vaginal fornix. The sample can include a fluid originating from the gynecological tract, such as a mucus secretion of the gynecological tract, such as cervico-vaginal fluid. In some embodiments, a sample can include a wash solution obtained from the gynecological tract. In particular embodiments, the sample is obtained from the cervix, the vagina, or the posterior vaginal fornix. In some embodiments, the sample is obtained from a cervical pap specimen. In some embodiments, the sample is substantially free of cells. In some embodiments, the sample is obtained using a method described in U.S. application Ser. No. 12/646,592, entitled "NOVEL MOLECULAR ASSAY AND USES THEREOF", the disclosure of which is incorporated herein by reference in its entirety.

Some embodiments include determining the level in the sample of at least 2 target molecules, at least 3 target molecules, at least 4 target molecules, at least 5 target molecules, at least 6 target molecules, at least 7 target molecules, at least 8 target molecules, at least 9 target molecules, at least 10 target molecules, at least 11 target molecules, at least 12 target molecules, at least 13 target molecules, at least 14 target molecules, at least 15 target molecules, at least 16 target molecules, at least 17 target molecules, at least 18 target molecules, at least 19 target molecules, or at least 20 target molecules.

Some embodiments also include comparing the level of at least one target molecule in a sample of a subject with the level of the target molecule in a sample from a subject without the cancer. Some embodiments also include comparing the level of at least one target molecule in a sample of a subject with the level of the target molecule in a sample from a subject with the cancer. Some embodiments include comparing the level of at least one target molecule in a sample of a subject with a reference level known to be indicative of a cancer or a lack of cancer.

In some embodiments, an increase in the level of the target molecule in a sample from a subject compared to the level of the target molecule in a sample from said subject without the cancer or a reference level known to be indicative of a cancer or a lack of cancer is indicative of the presence of the cancer in the subject. In some such embodiments, the target molecule can include a polypeptide or a fragment thereof, a nucleic acid encoding the polypeptide or fragment thereof, in which the polypeptide includes SEQ ID NOs.:9-33. In some embodiments, the polypeptide is an albumin protein fragment having a mass selected from the group consisting of about 2044, about 2098, about 2070, about 1013, about 1067, about 1639, about 999, about 1342, about 1396, about 1149, about 1405, about 1757, about 952, about 1169, about 1303, about 1623, about 1677, about 2403, about 2457, about 2413, about 2467, about 2541, about 2595, about 2559, about 2613, about 2720, about 2774, about 2916, about 2970, about 3362, about 3415 and about 1396. In some such embodiments, the polypeptide comprises at least one residue associated with iron.

In some embodiments, the cancer comprises endometrial cancer and the polypeptide includes SEQ ID NOs.:9-12 or SEQ ID NOs.: 24-33. In some embodiments, the cancer comprises endometrial cancer and the polypeptide is an albumin protein fragment having a mass selected from the group consisting of about 1013, about 1067, about 1396, about 1623, about 1677, about 1639, about 2044, about 2098, about 2403, about 2457, about 2413, about 2467, about 2541, about 2595, about 2559, about 2613, about 2720, about 2774, about 2916, about 2970, about 3362, about 3415 and about 1396. In some such embodiments, the polypeptide comprises at least one residue associated with iron.

In some embodiments, the cancer comprises ovarian cancer and the polypeptide includes SEQ ID NOs.:11-21. In some embodiments, the cancer comprises ovarian cancer and the polypeptide is an albumin protein fragment having a mass selected from the group consisting of about 2044, about 2098, about 2070, about 1639, about 999, about 1342, about 1396, about 1149, about 1405, about 1757, about 952, about 1169, and about 1303. In some such embodiments, the polypeptide comprises at least one residue associated with iron.

In some embodiments, a decrease in the level of the target molecule in a sample from a subject compared to the level of the target molecule in a sample from said subject without the cancer or a reference level known to be indicative of a cancer or a lack of cancer is indicative of the presence of the cancer in the subject. In some embodiments, the target molecule can include a polypeptide or a fragment thereof, a nucleic acid encoding the polypeptide or fragment thereof. In some embodiments, the cancer comprises endometrial cancer. In some embodiments, the cancer comprises ovarian cancer.

In some embodiments, an increase in the level of a target molecule in a sample compared to the level of the target molecule in a sample obtained from a subject without a cancer or a reference level known to be indicative of a cancer or a lack of cancer is indicative of the cancer, in which the increase is at least about a 3-fold increase at least about a 5-fold increase, at least about a 10-fold increase, at least about a 20-fold increase, at least about a 30-fold increase, at least about a 40-fold increase, at least about a 50-fold increase, at least about a 60-fold increase, at least about a 70-fold increase, at least about a 80-fold increase, at least about a 90-fold increase, and at least about a 100-fold increase.

In some embodiments, a decrease in the level of a target molecule in a sample compared to the level of the target molecule in a sample obtained from a subject without a cancer or a reference level known to be indicative of a cancer or a lack of cancer is indicative of the cancer, in which the decrease is at least about a 3-fold decrease at least about a 5-fold decrease, at least about a 10-fold decrease, at least about a 20-fold decrease, at least about a 30-fold decrease, at least about a 40-fold decrease, at least about a 50-fold decrease, at least about a 60-fold decrease, at least about a 70-fold decrease, at least about a 80-fold decrease, at least about a 90-fold decrease, and at least about a 100-fold decrease.

Methods to determine the level of a target molecule in a sample are well known in art. Some examples of such methods are provided herein. In some embodiments, a method for determining the level of a target molecule, such as a polypeptide or fragment thereof, can include an immunoassay. Examples of an immunoassay include a Western blot, an enzyme linked immunoabsorbent assay (ELISA), flow through assays, test strips, and radioimmunoassay. In some embodiments, a method for determining the level of a target molecule, such as a polypeptide or fragment thereof, can include mass spectrometry.

In some embodiments, the cancer is a non-cervical cancer of the gynecological tract. Examples of such cancers include endometrial cancer and ovarian cancer. As used herein, the term "endometrial cancer" refers to, but is not limited to endometrial carcinomas and endometrial adenocarcinomas. Endometrial cancers as used herein also include other well-known cell types such as papillary serous carcinoma, clear cell carcinoma, papillary endometrioid carcinoma, and mucinous carcinoma. Endometrial cancers also include endometrial hyperplasia, endometrial hyperplasia with atypia, and non-invasive endometrial cancer. As used herein, the term "ovarian cancer" refers to, but is not limited to ovarian tumors, carcinomas, (e.g., carcinoma in situ, invasive carcinoma, metastatic carcinoma) and pre-malignant conditions. By "ovarian tumor" is meant both benign and malignant tumors, such as ovarian germ cell tumors, e.g. teratomas, dysgerminoma, endodermal sinus tumor and embryonal carcinoma, and ovarian stromal tumors, e.g. granulosa, theca, Sertoli, Leydig, and collagen-producing stromal cells. Ovarian cancers as used herein also include art recognized histological tumor types, which include, for example, serous, mucinous, endometrioid, and clear cell tumors. The term ovarian cancer as used herein further includes art recognized grade and stage scales: grade I, II and III and stage I (including stage IA, IB and IC), II (including stage IIA, IIB and IIC), III (including stage IIIA, IIIB and IIIC), and IV.

In some embodiments, the subject is mammalian, for example, human.

Kits

Some embodiments include a kit for determining the presence or absence of a cancer in a female subject. In some such embodiments, the kit can include (a) a suitable diluent for irrigating the uterine cavity of the subject; (b) a receptacle for collection of the diluted uterine fluid; and (c) an agent that selectively binds to at least one target molecule. In some embodiments, the target molecule comprises a polypeptide or fragment thereof, or a nucleic acid encoding a polypeptide or fragment thereof. In some such embodiments, the polypeptide includes one of SEQ ID NOs.:9-33. In some embodiments, the polypeptide is an albumin protein fragment having a mass selected from the group consisting of about 2044, about 2098, about 2070, about 1013, about 1067, about 1639, about 999, about 1342, about 1396, about 1149, about 1405, about 1757, about 952, about 1169, about 1303, about 1623, about 1677, about 2403, about 2457, about 2413, about 2467, about 2541, about 2595, about 2559, about 2613, about 2720, about 2774, about 2916, about 2970, about 3362, about 3415 and about 1396. In some such embodiments, the polypeptide comprises at least one residue associated with iron.

Some kits include at least three agents that each selectively bind to a different target molecule, such as a polypeptide or a nucleic acid encoding said polypeptide. Some kits include at least five agents that each selectively bind to a different target molecule, such as a polypeptide or a nucleic acid encoding said polypeptide. Some kits include at least ten agents that each selectively bind to a different target molecule, such as a polypeptide or a nucleic acid encoding said polypeptide. In some embodiments, the agent comprises an antibody or fragment thereof.

In some embodiments, a kit comprises a molecule which selectively binds to a polypeptide comprising a sequence selected from SEQ ID NOs.:9-33 or a fragment thereof, a nucleic acid encoding a polypeptide selected from SEQ ID NOs.:9-33 or a fragment thereof, or an albumin protein fragment having a mass selected from the group consisting of about 2044, about 2098, about 2070, about 1013, about 1067, about 1639, about 999, about 1342, about 1396, about 1149, about 1405, about 1757, about 952, about 1169, about 1303, about 1623, about 1677, about 2403, about 2457, about 2413, about 2467, about 2541, about 2595, about 2559, about 2613, about 2720, about 2774, about 2916, about 2970, about 3362, about 3415 and about 1396, affixed to a solid support. In some embodiments, a kit comprises a plurality of molecules which selectively bind to a plurality of polypeptides selected from the group consisting of polypeptides comprising a sequence selected from the group consisting of SEQ ID NOs.:9-33 or a fragment thereof, a nucleic acid encoding a polypeptide selected from SEQ ID NOs.:9-33 or a fragment thereof, or comprising an albumin protein fragment having a mass selected from the group consisting of about 2044, about 2098, about 2070, about 1013, about 1067, about 1639, about 999, about 1342, about 1396, about 1149, about 1405, about 1757, about 952, about 1169, about 1303, about 1623, about 1677, about 2403, about 2457, about 2413, about 2467, about 2541, about 2595, about 2559, about 2613, about 2720, about 2774, about 2916, about 2970, about 3362, about 3415 and about 1396, affixed to a solid support. In some embodiments, a kit can also include a detectable agent which selectively binds to a target molecule.

Some embodiments include a kit comprising an agent which selectively binds to at least one polypeptide comprising an amino acid sequence selected from the group consisting of SEQ ID NOs.:9-33 or a fragment thereof, or comprising an albumin protein fragment having a mass selected from the group consisting of about 2044, about 2098, about 2070, about 1013, about 1067, about 1639, about 999, about 1342, about 1396, about 1149, about 1405, about 1757, about 952, about 1169, about 1303, about 1623, about 1677, about 2403, about 2457, about 2413, about 2467, about 2541, about 2595, about 2559, about 2613, about 2720, about 2774, about 2916, about 2970, about 3362, about 3415 and about 1396, wherein said agent is attached to a solid support. In some embodiments, a plurality of agents that bind to different polypeptides comprising a plurality of amino acid sequences selected from the group consisting of SEQ ID NOs.:9-33 or a fragment thereof, or different polypeptides comprising an albumin protein fragment having a mass selected from the group consisting of about 2044, about 2098, about 2070, about 1013, about 1067, about 1639, about 999, about 1342, about 1396, about 1149, about 1405, about 1757, about 952, about 1169, about 1303, about 1623, about 1677, about 2403, about 2457, about 2413, about 2467, about 2541, about 2595, about 2559, about 2613, about 2720, about 2774, about 2916, about 2970, about 3362, about 3415 and about 1396, are attached to said solid support. In some embodiments, the solid support comprises a solid phase test strip. Some embodiments also include a detectable agent which selectively binds to said polypeptide.

Some embodiments include a kit comprising an agent which selectively binds to at least one nucleic acid encoding a polypeptide comprising an amino acid sequence selected from the group consisting of SEQ ID NOs.:9-33 or a fragment thereof, or encodes an albumin protein fragment having a mass selected from the group consisting of about 2044, about 2098, about 2070, about 1013, about 1067, about 1639, about 999, about 1342, about 1396, about 1149, about 1405, about 1757, about 952, about 1169, about 1303, about 1623, about 1677, about 2403, about 2457, about 2413, about 2467, about 2541, about 2595, about 2559, about 2613, about 2720, about 2774, about 2916, about 2970, about 3362, about 3415 and about 1396, wherein said agent is attached to a solid support. In some embodiments, a plurality of agents that bind to a plurality of nucleic acids encoding different polypeptides comprising an amino acid sequence selected from the group consisting of SEQ ID NOs.:9-33 or a fragment thereof, or encoding different polypeptides comprising an albumin protein fragment having a mass selected from the group consisting of about 2044, about 2098, about 2070, about 1013, about 1067, about 1639, about 999, about 1342, about 1396, about 1149, about 1405, about 1757, about 952, about 1169, about 1303, about 1623, about 1677, about 2403, about 2457, about 2413, about 2467, about 2541, about 2595, about 2559, about 2613, about 2720, about 2774, about 2916, about 2970, about 3362, about 3415 and about 1396, are attached to said solid support. In some embodiments, the solid support comprises a solid phase test strip. Some embodiments also include a detectable agent which selectively binds to said polypeptide.

Some embodiments of the methods and compositions provided herein include isolated polypeptides consisting essentially of an amino acid sequence selected from the group consisting of SEQ ID NOs.:9-33 or a fragment thereof, or of an albumin protein fragment having a mass selected from the group consisting of about 2044, about 2098, about 2070, about 1013, about 1067, about 1639, about 999, about 1342, about 1396, about 1149, about 1405, about 1757, about 952, about 1169, about 1303, about 1623, about 1677, about 2403, about 2457, about 2413, about 2467, about 2541, about 2595, about 2559, about 2613, about 2720, about 2774, about 2916, about 2970, about 3362, about 3415 and about 1396, wherein said polypeptide is differentially expressed in cancer. Some embodiments of the methods and compositions provided herein include isolated polypeptides consisting of an amino acid sequence selected from the group consisting of SEQ ID NOs.:9-33 or a fragment thereof, or of an albumin protein fragment having a mass selected from the group consisting of about 2044, about 2098, about 2070, about 1013, about 1067, about 1639, about 999, about 1342, about 1396, about 1149, about 1405, about 1757, about 952, about 1169, about 1303, about 1623, about 1677, about 2403, about 2457, about 2413, about 2467, about 2541, about 2595, about 2559, about 2613, about 2720, about 2774, about 2916, about 2970, about 3362, about 3415 and about 1396, wherein said polypeptide is differentially expressed in cancer.

Some embodiments of the methods and compositions provided herein include isolated nucleic acids encoding a polypeptide consisting essentially of an amino acid sequence selected from the group consisting of SEQ ID NOs.:9-33 or a fragment thereof, or of an albumin protein fragment having a mass selected from the group consisting about 2044, about 2098, about 2070, about 1013, about 1067, about 1639, about 999, about 1342, about 1396, about 1149, about 1405, about 1757, about 952, about 1169, about 1303, about 1623, about 1677, about 2403, about 2457, about 2413, about 2467, about 2541, about 2595, about 2559, about 2613, about 2720, about 2774, about 2916, about 2970, about 3362, about 3415 and about 1396, wherein said polypeptide is differentially expressed in cancer. Some embodiments of the methods and compositions provided herein include isolated nucleic acids encoding a polypeptide consisting of an amino acid sequence selected from the group consisting of SEQ ID NOs.:9-33 or a fragment thereof, or of an albumin protein fragment having a mass selected from the group consisting of about 2044, about 2098, about 2070, about 1013, about 1067, about 1639, about 999, about 1342, about 1396, about 1149, about 1405, about 1757, about 952, about 1169, about 1303, about 1623, about 1677, about 2403, about 2457, about 2413, about 2467, about 2541, about 2595, about 2559, about 2613, about 2720, about 2774, about 2916, about 2970, about 3362, about 3415 and about 1396, wherein said polypeptide is differentially expressed in cancer.

Some embodiments of the methods and compositions provided herein include isolated agents that selectively bind to an isolated polypeptide consisting of an amino acid sequence selected from the group consisting of SEQ ID NOs.:9-33 or a fragment thereof, or of an albumin protein fragment having a mass selected from the group consisting of about 2044, about 2098, about 2070, about 1013, about 1067, about 1639, about 999, about 1342, about 1396, about 1149, about 1405, about 1757, about 952, about 1169, about 1303, about 1623, about 1677, about 2403, about 2457, about 2413, about 2467, about 2541, about 2595, about 2559, about 2613, about 2720, about 2774, about 2916, about 2970, about 3362, about 3415 and about 1396, wherein said polypeptide is differentially expressed in cancer. In some such embodiments, the agent comprises an antibody or fragment thereof.

EXAMPLES

Example 1—Identification of Iron-Modified Polypeptides

Serum markers have long been investigated for early detection of endometrial cancer; however, these are highly diluted and generally non-specific. In order to enhance specificity of detection of endometrial cancer, Applicants have developed a novel proteomic-based screening test based on sampling from site-specific sources, such as the mucus of the cervix and vagina. Such readily available mucus samples contain an abundance of proteins and can be obtained via methods similar to a routine PAP smear. FIG. 1 shows an embodiment of a collection method using a cervical brush to obtain a sample from the cervix of a subject.

Applicant has identified by comparing the protein differences between endometrial cancer patients and normal healthy controls a statistically significant group of proteins that have undergone iron adduct modifications. These peptides either alone or in combination form an endometrial cancer "fingerprint" that is useful in distinguishing endometrial cancer from normal controls.

Methods

Samples from over 1,000 patients were collected according to a USA IRB approved prospective study (USA IRB #09-034). Methods of collection are described in Example 2, and in U.S. Ser. No. 12/646,592, incorporated by reference herein in its entirety.

Proteomic Analysis

High resolution MS and MS/MS data were obtained by injecting samples into a nano-LC-LTQ-Orbitrap mass spectrometer. Raw data files were converted into search files using Xcalibur software, which were then searched using a search engine such as Mascot. The Mascot search engine (Matrix Science Ltd, London, UK) was used to identify polypeptides useful in screening endometrial cancer. All data in DifProWare was searched against the July 2009 downloaded version of the RefSeq protein database from NIH using the Mascot search engine. Parameters used to assign protein identification were taxonomy *Homo sapiens*, trypsin enzyme with up to 2 missed cleavages, possible deamidation, 10 ppm error in mass (MS) and 0.6 Da in sequence data (MS/MS), instrument ESI-TRAP and auto reporting.

A series of peptides that varied in intensity between individuals but that appeared to correlate to the physical status of the individual gave relatively clean spectra but did not assign to any standard modification. They also did not match during an error tolerant search performed with the Mascot search system. These peptides of interest were examined further by de novo sequencing (manual interpretation of the MS/MS sequence spectra) and each contained a "peptide gap" that did not match the expected mass from any of the standard amino acids. These spectra were observed in many samples and multiple biological fluids, therefore, a method to average and deconvolute the average spectra to the +1 charge state was developed. Spectra were selected based on peptide masses that eluted at from the reverse phase column at the same retention time (after time LC alignment) and that had the same peptide mass to better than 5 ppm. The amino acids mass gaps were calculated and determined manually but tentative sequences were put into the peptide sequence software of the Waters MassLynx programs (Waters. Milford Mass.). Amino acid gaps were found in the series of spectra that did not match a standard mass gap and it was observed that these gaps were mass deficient, hence showing mass gaps that were less than an integer by as much as 0.1 Da. A careful examination showed that these amino acid mass gaps corresponded to a known amino acid mass plus approximately 53.9 Da. This was found to be a metal adduct and further examination of the UniMod database indicated that iron modification minus two hydrogens was a possibility, and present on acidic amino acids such as aspartic acid and glutamic acid.

For the validation and characterization of the iron (Fe) adducts, proteins were isolated from the specimens by overnight acetone precipitation and chromatographic fractionation with reverse phase HPLC. The protein pellets and fractions were dried by centrifugal lyophilization (Savant, USA), followed by dilution into a 50 µL solution of 50 mM ammonium bicarbonate (ABC) and 10 mM tris(2-carboxyethyl)phosphine (TCEP). In parallel, some samples were directly digested after dilution in ABC/TCEP without protein isolation. Samples were then digested overnight in 37° C. shaker with 1 µl of sequencing grade Promega trypsin. Samples were centrifuged at 13,200 rpm for 15 minutes. The supernatant was removed and placed into a mass spec vial for further analysis.

Statistical Analysis

Blinded proteomic data was evaluated statistically. Statistical methods to identify polypeptides for use as biomarkers and to prioritize such polypeptides for such use are described in Yasui, Y., et al., "A data-analytic strategy for protein biomarker discovery: profiling of high dimensional proteomic data for cancer detection." *Biostatistics,* 2003. 4:449-63, which is incorporated herein by reference in its entirety. All data processed through statistical analysis was derived from a DifProWare analysis of the peptides discovered by Mass Spectrometry of individualized samples. Data analysis was conducted by: (i) performing separate biomarker screening for normalized and un-normalized data; (ii) screening peaks using Fisher's exact test, Wilcoxon rank-sum (non-parametric t-test) and area under the curve (AUC); (iii) reporting fold-difference for each peak between groups; and (iv) using a false discovery rate (FDR) to set "difference" thresholds to identify peptides for further analysis. After normalization, several summary statistics were used to evaluate each peptide's ability to distinguish endometrial cancer from control specimens. A protein of a statistically significant endometrial cancer "fingerprint" specific for endometrial cancer includes an identified polypeptide that exceeded both the 5% false discovery rate threshold and the Fisher's test threshold.

Results

Data Source and Processing

Three LC-MS runs were performed for each patient sample. Peptide peak areas were normalized using the 80th percentile matching. Peptides with zero peak areas were assumed to be below the limit of quantification (BQL). Zero areas were replaced with ½ the minimum reported peak area for the corresponding peptide. Peak areas were subsequently log 10 transformed, and averaged across the three runs for each patient. Thus, each patient's data contributed to the data analysis a single (log 10) average peak area for each peptide. Modified-to-unmodified peptide ratios were computed separately for each LC-MS run, after replacement of BQL values. Ratios were subsequently log 10 transformed and averaged for each patient.

Statistical Modeling Approach

The primary method used for statistical model selection was the "lasso" method, with penalty factor chosen by leave-one-out cross-validation LOOCV (with minimum deviance criterion) (Tibshirani, R. Regression Shrinkage and Selection via the Lasso. *J. Roy. Statist. Soc. Ser. B.* 1996; 58:267-288). The lasso method selects a parsimonius set of predictors from a large set of potential predictors, and includes a coefficient "shrinkage" estimation method to prevent overfitting training data, therefore improving prediction in independent test data sets. The lasso method is a penalized likelihood method in which the final number of selected predictors and their model coefficient shrinkage is controlled by a single penalty parameter. For the following analyses, the penalty parameter was selected using leave-one-out cross validation (LOOCV).

LOOCV selects the statistical model which best predicts the outcome of each "hold-out" observation. A patient sample is selected, and temporarily held-out of the training data. A statistical model is fit to the training data, and the resulting parameter estimates are used to predict the value of the hold-out observation. The process is repeated for each sample (patient) in the data set. The penalty parameter with the best hold-out predictive performance is retained for fitting the entire dataset. The criterion for evaluating hold-out predictive performance is logistic model deviance.

A secondary method of model selection, best subsets regression, was also used for the different peptide groups. This procedure exhibits very different operating characteristics than lasso, and is included to provide alternative modeling results. Best subsets regression examines all possible subsets of potential predictors, and selects the predictor set maximizing cross validation performance. This procedure tends to produce smaller statistical models (i.e., fewer predictors), but with larger estimated coefficients (no coefficient shrinkage). Thus, the fitted coefficients may overpredict in independent test data.

Iron Modified Peptides

Six peptides from albumin were selected. The mass/time values for these are shown in Table 1. Peptides with mass about 2097 and 2098 are modified versions of the peptide with mass about 2044. These differed only in that they contain differing levels of iron (Fe) isotopes. Similarly, the peptide at 1066 was likely to be a modified version of the 1012 peptide. In the analyses that follow, each of the six peptides were considered separately, as a potential predictor. In addition, combinations of signals, based on the putative modified:unmodified relationships were considered. These combinations are listed in Table 2.

TABLE 1

| Mass | Time |
| --- | --- |
| 2098.01 | 52.99 |
| 2044.09 | 53.00 |
| 2097.01 | 52.97 |
| 1066.51 | 41.81 |
| 1012.59 | 42.11 |
| 1638.93 | 35.12 |

TABLE 2

| Name | Combination of peptides |
| --- | --- |
| aggregate 1 | sum of 2097 and 2098 peptide signals |
| ratio 1 | 2098 signal/2044 signal |
| ratio 2 | 2097 signal/2044 signal |

TABLE 2-continued

| Name | Combination of peptides |
| --- | --- |
| ratio 3 | (2097 + 2044)/2044 signal |
| ratio 4 | 1066 signal/1012 signal |

Thus, there are a total of 11 potential albumin peptide predictors (6 peptides, 5 composite signals). The modeling approach selected four peptide signals for predicting endometrial cancer. These signals and their estimated coefficients are shown in the Table 3.

TABLE 3

| Peptide | Coefficient | Odds factor |
| --- | --- | --- |
| (Intercept) | −8.63 | |
| X2098 | 0.93 | 2.53 |
| X2044 | 0.01 | 1.01 |
| X1012 | 0.46 | 1.58 |
| X1639 | 0.33 | 1.39 |

Modeling results
Null deviance −= 141.36
Fitted model dev = 84.78
Difference dev = 56.59
Model p-value = 1.510791e−11
AUC = 0.9

The selected albumin peptides predicted endometrial cancer substantially better than random chance. The regression coefficients indicated that increases in any of the selected peptide peak areas were associated with increasing odds of endometrial cancer. Note that peptide X2098 had the strongest effect on odds of endometrial cancer. The odds of endometrial cancer increased by a multiplicative factor of 2.5 (exp (0.93)) for every 10-fold increase in peptide 2098 peak area. Conversely, the coefficient for X2044 was near 1, and appeared to have little effect on odds. It is possible that the inclusion of this peptide was an artifact of a model selection technical constraint. Nevertheless, model performance on LOOCV was improved by its inclusion. The area under the receiver operating characteristic curve (AUC) was 0.9. The best subsets approach identified a statistical model with only the peptide at mass 2098 as a predictor. The fitted values from this model resulted in an AUC value of 0.88. The coefficients in the logistic regression model are shown in Table 4.

TABLE 4

|  | Estimate | Std. Error | z value | PR(>\|z\|) |
| --- | --- | --- | --- | --- |
| (Intercept) | −5.94 | 1.13 | −5.24 | 0.00 |
| X2098 | 1.51 | 0.29 | 5.21 | 0.00 |

Figure 2:
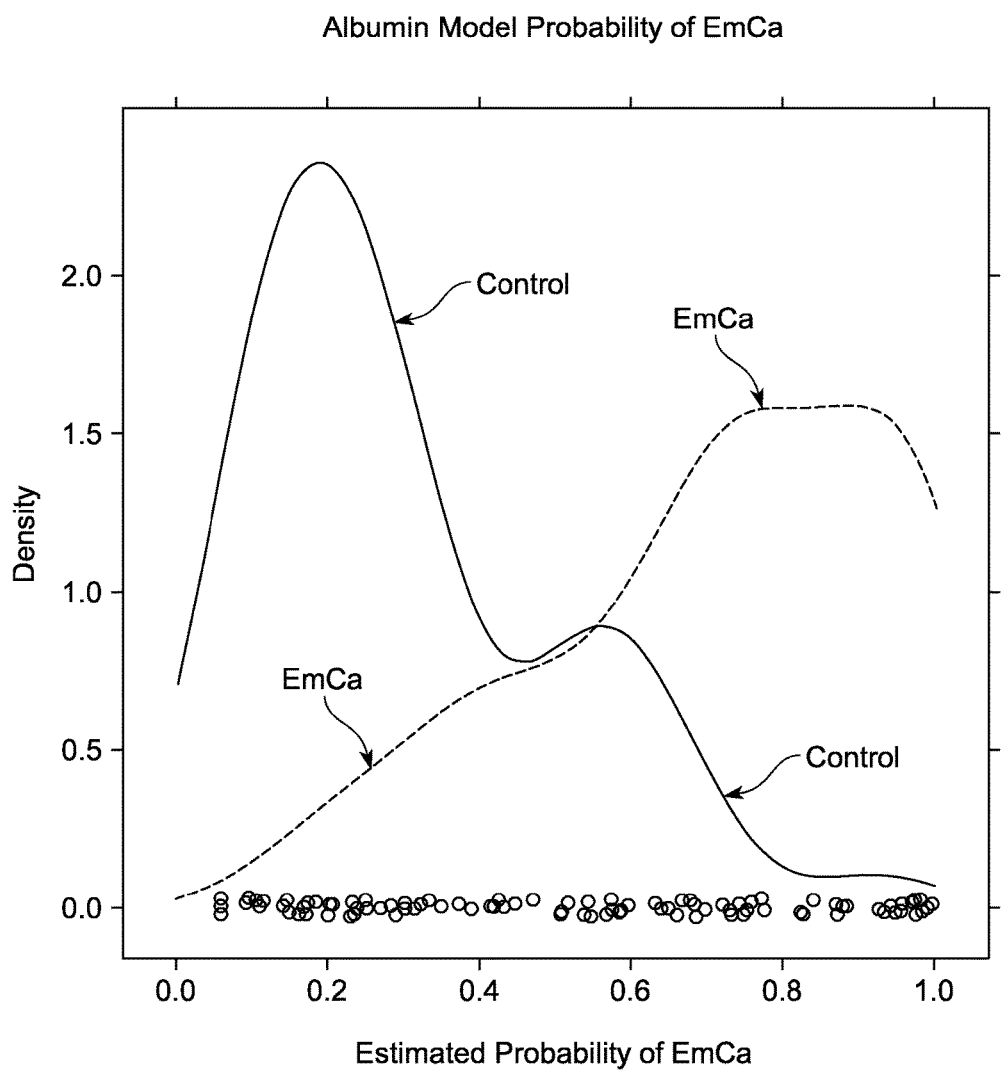
FIG. 2 is a graph showing the distribution of fitted probabilities of endometrial cancer (EmCa) for control and diseases patients, in particular, the probabilities from lasso logistic regression using albumin peptides 2098, 2044, 1012, and 1639. Circles denote individual patient's estimated probabilities using the albumin peptide model. The curved lines denote estimated probability distributions for control and EmCa groups.
Figure 3:
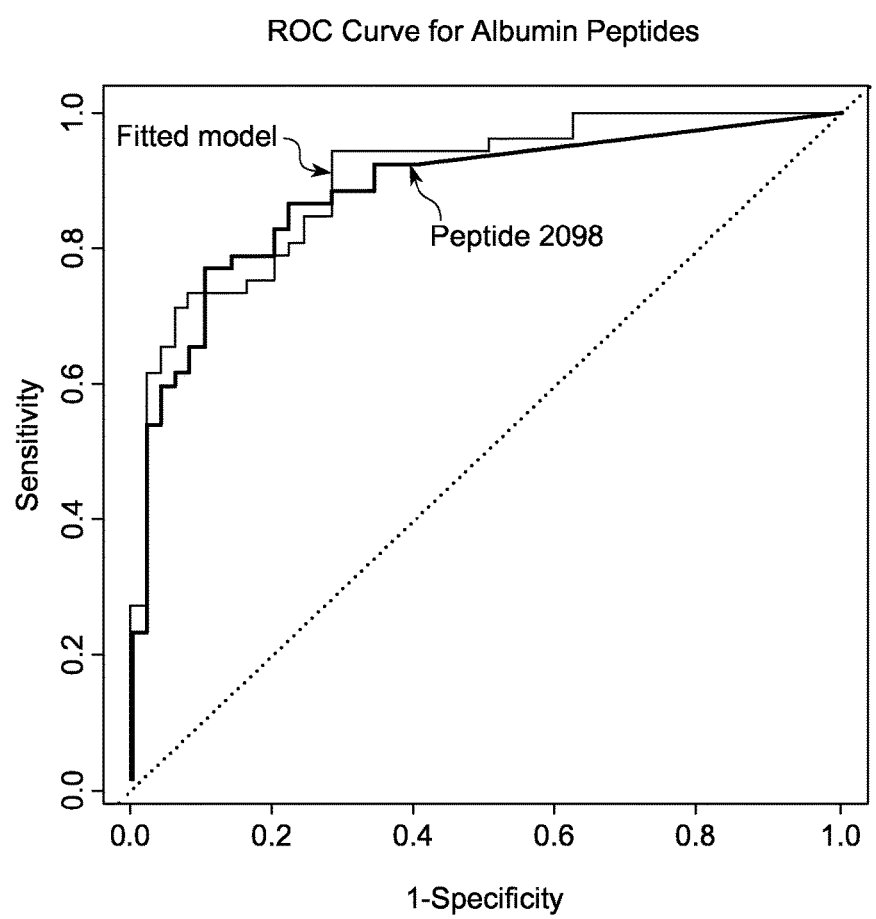
FIG. 3 is a graph showing the receiver operating characteristic curve for albumin peptides 2098 alone (AUC=0.88). The modeling results did not significantly improve the AUC from peptide 2098 alone.

FIG. 2 is a graph showing the distribution of fitted probabilities of endometrial cancer (EmCa) for control and diseases patients, in particular, the probabilities from lasso logistic regression using albumin peptides 2098, 2044, 1012, and 1639. Circles denote individual patient's estimated probabilities using the albumin peptide model. The curved lines denote estimated probability distributions for control and EmCa groups. FIG. 3 is a graph showing the receiver operating characteristic curve for albumin peptides 2098 alone (AUC=0.88). The modeling results did not significantly improve the AUC from peptide 2098 alone.

Modified Peptides

Nine peptides with post-translational modifications were selected from analysis. The mass and retention times for these peptides are shown in Table 5.

TABLE 5

| Mass | Time |
| --- | --- |
| 1212.67 | 69.38 |
| 3370.54 | 22.39 |
| 1431.61 | 29.81 |
| 3661.64 | 22.75 |
| 3049.40 | 59.55 |
| 2996.46 | 53.07 |
| 1367.57 | 30.71 |
| 2098.01 | 52.99 |
| 1066.51 | 41.81 |

The lasso-CV procedure identified the following peptides for inclusion in the statistical model shown in Table 6.

TABLE 6

| Peptide | Coefficient | Odds factor |
| --- | --- | --- |
| (Intercept) | −13.22 | |
| X1213 | 0.41 | 1.50 |
| X3662 | 2.37 | 10.68 |
| X3049 | 0.27 | 1.30 |
| X2996 | 0.37 | 1.45 |
| X2098 | 0.36 | 1.43 |
| X1067 | 0.46 | 1.59 |

Modeling results
Null deviance −= 141.36
Fitted model dev = 77.73
Difference dev = 63.63
Model p-value = 8.194223e−12
AUC = 0.95

Figure 4:
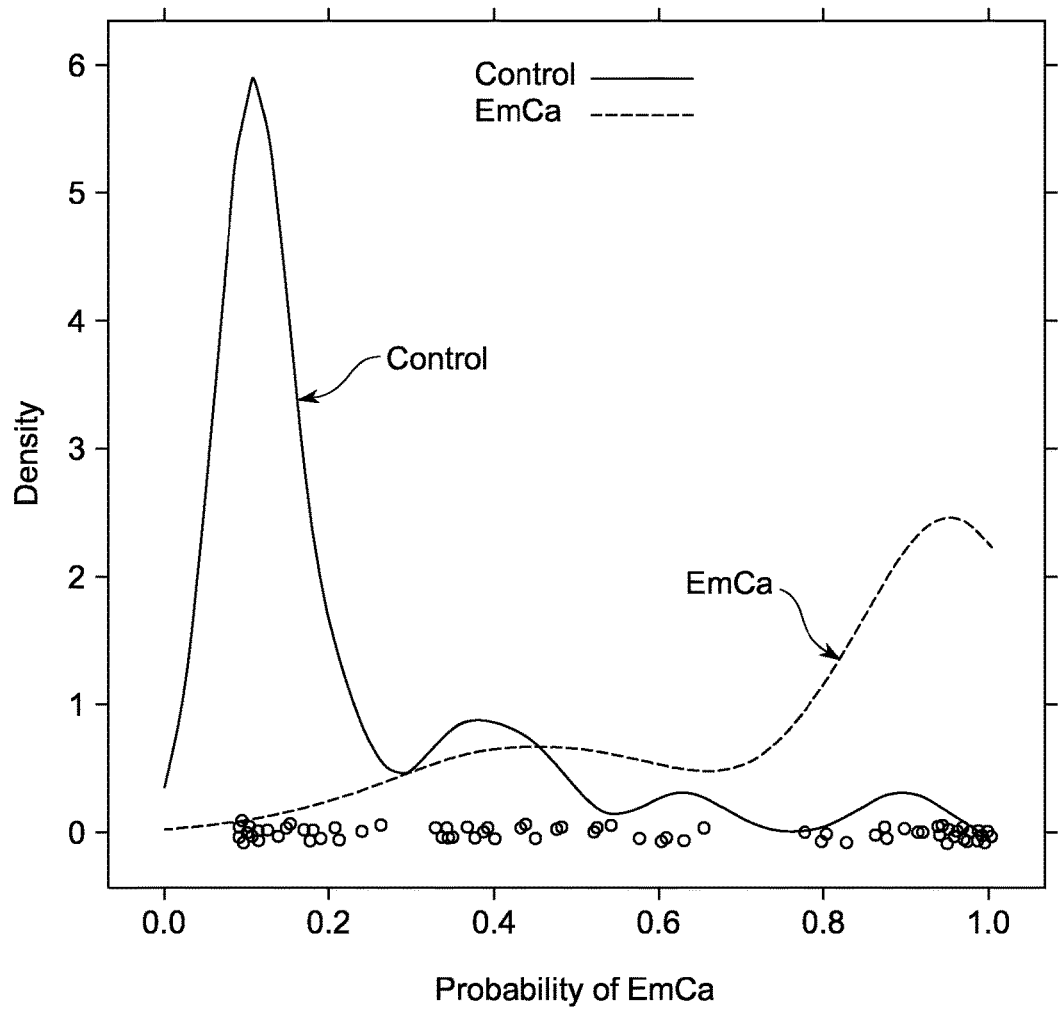
FIG. 4 is a graph showing the distribution of fitted probabilities of endometrial cancer (EmCa) for control and diseases patients.
Figure 5:
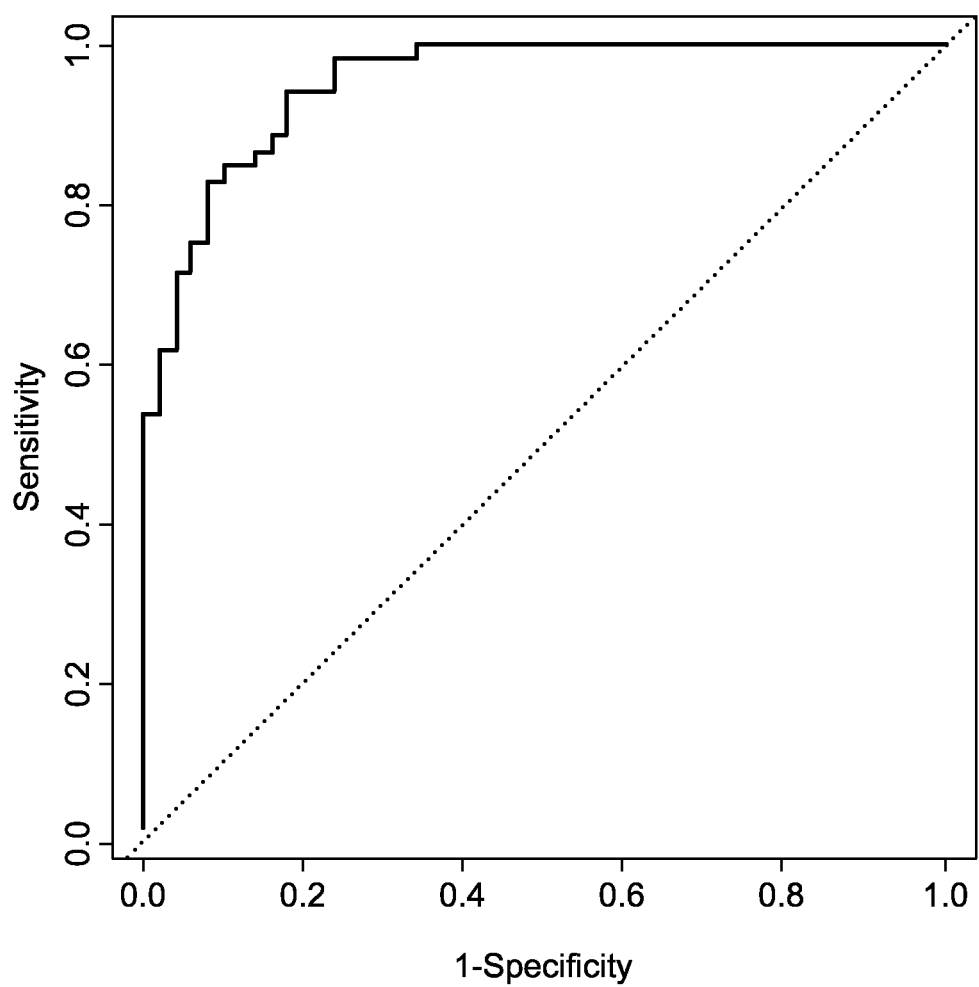
FIG. 5 is a graph showing the receiver operating characteristic curve for for control and diseases patients.

Five modified peptides were selected for inclusion in the lasso logistic regression model. All were positively associated with increased probability of endometrial cancer. This collection of peptides was strongly associated with separation of control and endometrial cancer patient samples (p~10e-12) and an AUC of 0.95. The best subsets procedure identified a statistical model with two peptide predictors as masses about 3662 and 3049. The coefficients in the logistical regression model are shown in Table 7. The fitted values for this model results in an AUC value of 0.93. FIG. 4 and FIG. 5 illustrate the distributions and ROC curve for model estimated probabilities for control and endometrial cancer patients.

TABLE 7

|  | Estimate | Std. Error | z value | PR(>\|z\|) |
| --- | --- | --- | --- | --- |
| (Intercept) | −16.55 | 3.33 | −4.97 | 0.00 |
| X3662 | 4.53 | 1.11 | 4.07 | 0.00 |
| X3049 | 1.08 | 0.23 | 4.63 | 0.00 |

Discussion

With robust statistical modeling, the data provided herein demonstrates that the methods have a sensitivity and specificity that is significant to employ screening tests with an AUC of 0.88. As such, the novel detection of iron-modified polypeptides demonstrate a statistically significant fingerprint for the detection of endometrial cancer. Further, these modifications can be covalent or non-covalently bonded. Even with MS/MS spectra that show good intensity and apparent amino acid sequence ions, numerous peptide masses of interest within samples were listed in the unassigned peptide list that follows assigned proteins in a typical Mascot search result. These peptides may get reasonable scores, such as those shown in Table 8, but many have very poor individual scores and the assignments do not align other peptides from the same proteins. In general, these "orphan peptides" are ignored even though their spectra may appear to show the clear sequence ions.

sequences associated with it searched by either method, these sequences often matched back to abundant proteins in the digests as determined during the Mascot (database)

TABLE 8

| Query | Observed | Mr (expt) | Mr (calc) | ppm | Miss | Score | Expect | Rank | Peptide |
|---|---|---|---|---|---|---|---|---|---|
| 1113 | 679.3644 | 1356.7142 | 1356.7222 | -5.88 | 2 | 28 | 0.022 | 1 | QLSEDGRQLRR (SEQ ID NO: 01) |
| 652 | 572.8156 | 1143.6166 | 1143.6070 | 8.35 | 1 | 24 | 0.063 | 1 | GEMSGRLGPLK (SEQ ID NO: 02) |
| 651 | 572.8152 | 1143.6158 | 1143.6070 | 7.70 | 1 | 23 | 0.073 | 1 | GEMSGRLGPLK (SEQ ID NO: 02) |
| 339 | 503.2898 | 1004.5650 | 1004.5655 | -0.44 | 1 | 23 | 0.046 | 1 | QVEVKFQK (SEQ ID NO: 03) |
| 213 | 454.2660 | 906.5175 | 906.5174 | 0.08 | 1 | 22 | 0.039 | 1 | NLLEKYK (SEQ ID NO: 04) |
| 84 | 421.7582 | 841.5018 | 841.5021 | 0.39 | 1 | 22 | 0.058 | 1 | VAGAATPKK (SEQ ID NO: 05) |
| 252 | 465.2473 | 928.4801 | 928.4800 | 0.13 | 0 | 19 | 0.14 | 1 | IPACIAGER (SEQ ID NO: 06) |
| 91 | 421.7584 | 841.5023 | 841.5021 | 0.19 | 1 | 19 | 0.11 | 1 | LEKTVPR (SEQ ID NO: 07) |
| 90 | 421.7583 | 841.5021 | 841.5021 | 0.03 | 1 | 19 | 0.12 | 1 | LEKTVPT (SEQ ID NO: 08) |

During ongoing biomarker discovery analyses, a series of interesting peptides were identified that were not assignable to any acceptable peptide sequence with or without standard post-translational modifications. To assist in de novo sequencing, spectra were combined that came from common peptides as determined by elution time and mass. These common spectra were obtained identified across many samples that are part of ongoing studies. These averaged spectra (S/N enhanced) were then deconvoluted to the +1 charge state. A series of mass gaps were detected that were between 53.8 and 54 Da different from one of the standard amino acid sequences. This was based on the water losses and isotopes present. During the sequencing, the MassLynx peptide sequencing software was used to assist in the graphical display of the ion series as the individual averaged spectra were manually sequenced. Partial sequences of the peptides were obtained and these were then searched against a database of all the known proteins in the samples as determined by the Mascot search results. As a second method of identification, a search similar to the NCBI Blast search program was developed that was specifically tailored to manual, MS-based peptide sequencing. This allows for the addition of single amino acids to a partial sequence and provides the sequence of any proteins that have the matching sequences. It allows for the inefficiencies of the MS collisional fragmentation and its inability to distinguish like mass amino acids apart such as leucine and isoleucine. When the approximately 53.9 Da shift was identified and the search. It was observed that the unmodified peptides eluted close to the retention time of the Fe (iron) modified peptides.

Figure 6:
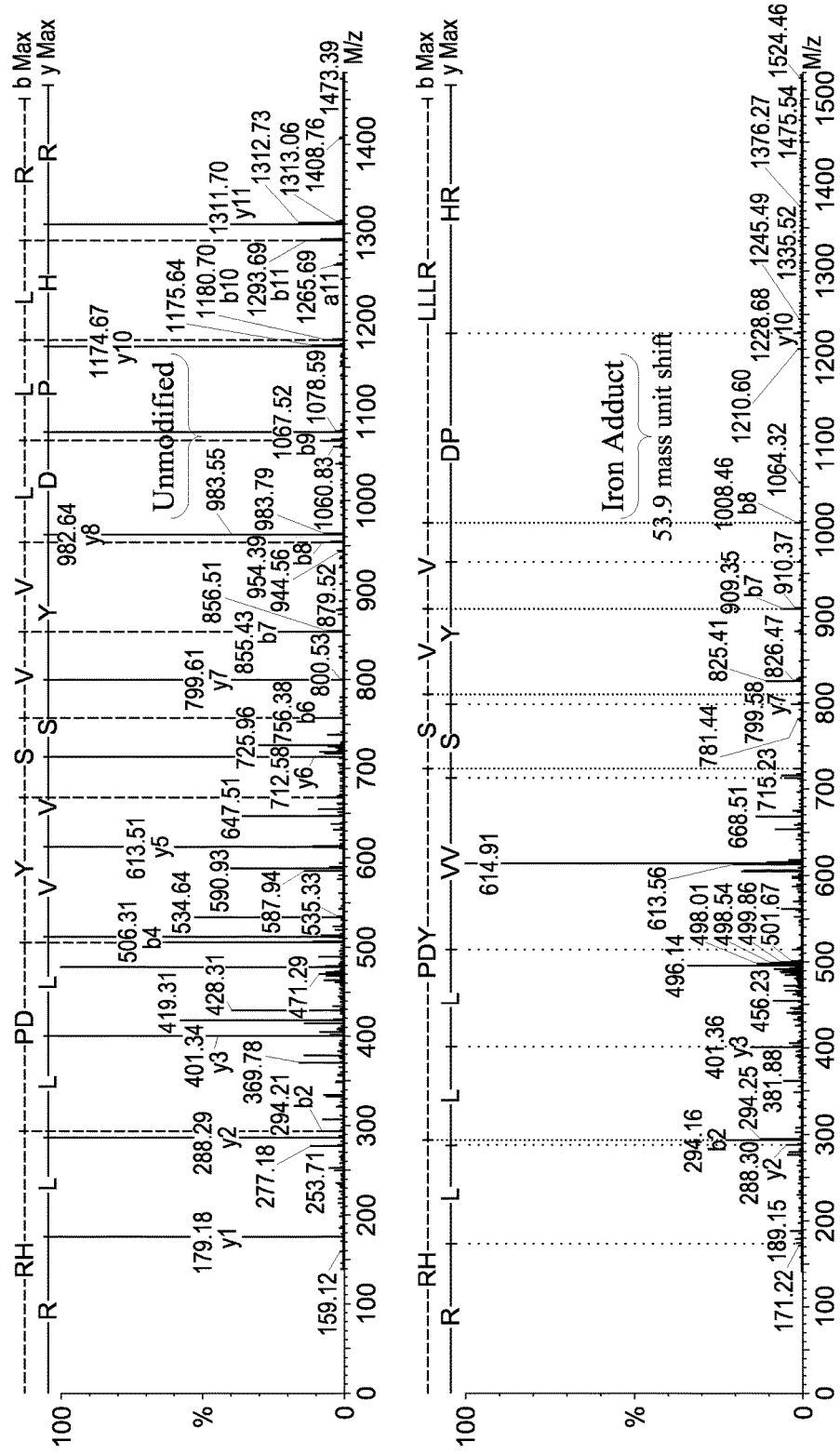
FIG. 6 shows spectra that include an albumin peptide determined by de novo sequencing. The spectra demonstrate the albumin peptide with and without a mass shift present. This tryptic peptide occurs on amino acid positions 361-372 of the protein, with both peptides sharing the same amino acid sequence.

FIG. 6 shows a spectra displaying an albumin peptide that was determined by de novo sequencing. These spectra demonstrate the albumin peptide with and without a mass shift present. This tryptic peptide occurs on amino acid positions 361-372 of the protein, with both peptides sharing the same amino acid sequence. The unmodified peptide has a molecular weight of 1466.835 Da, and the modified peptide has a molecular weight of 1520.753 Da, presenting a very obvious shift very close to the theoretical monoisotopic value of 53.919289 Da listed in UniMod. To confirm assignments and the presence of iron modifications on peptides and, thus proteins, individual and averaged spectra of the specific peptides using a variable modification of iron were searched.

While literature exists which suggests the ability of iron to bind to proteins, however no data exists that demonstrates that this modification can be utilized as a biomarker for malignancies, specifically gynecologic cancer (Quinlan, G., et al., T. Albumin: Biochemical Properties and Therapeutic Potential. *Hepatology*. 2005; 41:1211-1219). The Unimod listing suggested that these modifications are observed when acidic amino acids aspartic acid (D) and glutamic acid (E) are present, but the C-terminus is another possible site (http://www.unimod.org). An example of an iron modified C-terminal peptide fragment of albumin is shown in Table 9.

TABLE 9

| Start-End | Observed | Mr (expt) | Mr (calc) | ppm | Miss | Sequence | SEQ ID NO |
|---|---|---|---|---|---|---|---|
| 599-609 | 534.2634 | 1066.5122 | 1066.5110 | 1 | 0 | .LVAASQAALGL.- Iron (Ions score 52) | 09 |

While the peptide sequence of Table 9 was manually sequenced and determined to be from albumin, all assignments were confirmed by searching both the averaged and individual spectra of the single, modified peptide with Mascot using a variable modification of iron of the acidic groups (D, E and C-terminus) and this confirmed the assignments of the iron modified peptides. What also became apparent is that these iron adducts were not only associated with acidic residues and the variable modification term was adjusted to allow modification at any amino acid and the C-terminus.

Further proof of the presence of iron in these spectra, apart form the obvious mass and sequence ion shifts, could be seen in the isotope pattern of the peptide molecular weight ion. Iron has two major isotopes and ca. 55 and 56 Da and computer simulations resulting from the addition of the iron isotope pattern to the molecular ion of the unmodified peptide provide isotope patterns that matched the modified peptide molecular ions. This added further proof to the presence of iron in these peptides.

There have been many suggestions about the reversible modification of proteins by iron. It is true that in some biofluids, free iron may be present in the fluid and this could results in MS-derived adducts with peptides, similar to sodium adducts that can be detected in MS-spectra. While it is true that with acetone precipitation salts (including iron) may precipitate with the protein, proteomes that are desalted and carefully isolated by LC using high quality solvents should be free of iron, even iron attached to heme groups as they elute before the protein. The profiles of the iron adducts did not appear to vary with the isolation method, indicating that the iron was covalently bound to the peptides. In addition to the isolation method, all peptide digest samples were eluted into the LTQ-Orbitrap MS from a C-18 reverse phase column which provides an additional level of purification. From the observations provided herein, the iron modifications were not randomly located on the peptide backbones but on specific amino acids or limited sequences (if acidic residues present and close together). Therefore the iron modifications were located on specific residues in the proteins. Furthermore, in many human biofluids, human serum albumin is the major protein present and shows the highest level of modification with some sites being occupied at significant levels. However, other proteins including the globins, annexins, keratins and S100 proteins that are present at higher levels in samples were also shown to be modified. Thus, iron adducts may be present on many proteins but may often be at levels that are too low to detect by MS sequencing-based methods.

Example 2—Identification of Iron-Modified Polypeptides Associated with Gynecological Disorders: Sample Collection IRB approval was obtained (USA IRB #09-034 3/412009) according to institutional procedures for collection of cervico-vaginal secretions. Patients gave signed written consent to have these samples collected during routine pelvic examinations within the University of South Alabama (USA) and Mobile Infirmary Health System (MIMC) facilities. Samples were collected within the clinic space as well as operating rooms at each hospital. Patients aged 21 or older at time of informed consent who had a uterus were eligible for sample collection. Patients with prior hysterectomy, lack of clinical data, or lack of follow-up were excluded from this study. Physicians involved within the study collected data from chart review of clinic notes, operative reports, pathology reports and entered this information into a password protected centralized computerized database. Patients were initially categorized into categories based on information available at their initial presentation. These categories were broad and were further refined once final pathology was available. For example, a patient might initially be categorized as having an "ovarian cyst/pelvic mass". This would be entered into the database as the primary diagnosis. If, after having surgery, she was found to have ovarian cancer, endometriosis, and fibroids, all of these diagnoses would have been entered as the final diagnoses. Patients were grouped into more specific diagnostic categories based on their final histologic diagnosis such as: Endometrial cancer, Ovarian cancer, Endometriosis, Uterine Fibroids, Infertility, Pregnancy, benign pelvic mass, etc. These groups were subdivided into "pure" and "mixed" samples based on the absence or presence of alternative confounding diagnoses. Data variables included patient demographics, surgicopathologic data, cancer related data, and comorbid conditions. All clinical data was stripped of patient identifiers and coded with patient study number, sample number by the data coordinator and keep in a separate location. Researchers involved in the basic science aspect of the data analysis were blinded to patient identifiers. Samples were collected by IRB approved physicians within the USA and MIMC health system gynecologic clinics and/or within the operating room after anesthesia induction and prior to surgery. First, a dacron tipped swab was placed in the vaginal vault for approximately 15 seconds and then immediately placed within a preservative solution for storage/transport and labeled with sample number and code for vaginal sample. Second, a standard cytobrush was placed within the cervical os (in the endocervical canal) and turned several times, (identical to Pap smear techniques) and also placed within a preservative solution for storage/transport and labeled with sample number and code for cervical sample. For each patient in the study, a vaginal and cervical sample was obtained in both the clinic setting as well as the operating room setting for those who were undergoing surgery. For a small selected group of patients, a tampon collection was obtained. The patient was given a study tampon and was instructed to insert "x" hours before surgery/clinic. The tampon was removed by the physician and placed in the preservative solution as described herein. Other volunteers representing healthy controls with no gynecological diseases were also provided with tampons, and the volunteer placed the tampon into the vagina in the normal way and removed it after "x" minutes and placed into the provided liquid.

Coded samples were collected from clinic on a daily basis and logged into proteomic laboratory upon arrival. The liquid solution was further processed by centrifugation to remove all or substantially all of the cells and other debris so that the polypeptide analyses described herein involves the soluble proteins contained in the liquid solution; the cells and pellet were discarded. The resulting fluid was stored at −80 C until analysis. Proteins were isolated from the samples by dispersing approximately 1% of the sample into 0.1% trifluoroacetic acid (TFA). Proteins were eluted with 60% Acetonitrile (ACN) on an Agilent C3 pre-column using 2% ACN. Following overnight digestion with trypsin, the samples underwent a triplicate injection into a LTQ-Orbitrap MS with the injection volume based on the UV peak height from the chromatogram. The MS ran on one second scans (peptide mass data collected) with 5 per second MS/MS scans of selected peptide masses. Search files were combined and one large search was done for endometrial cancer patients versus normal controls. Individuals were then compared via their peptide sequence data using mascot search comparisons or DifProWare.

Example 3—Identification of Polypeptides Associated with Endometrial Cancer Identification of Polypeptides Data were acquired on an LTQ-Orbitrap mass spectrometer using input from an LC system. The A solvent contained 3% of B and 0.2% formic acid in water. The B solvent contained 3% of A and 0.2% formic acid in acetonitrile. Solvents were HPLC grade from Fisher. For a 120 min run, the starting solvent was 5% B and remains for 7 min. The gradient was changed to 10% by 13 min, 40% by 83 min, 90% by 103 min, then reduced from 90% to 5% at 111 min. It was then re-equilibrated for the next injection. Three injections were performed for each sample for repeatability determination.

The MS was scanned (Orbitrap) over the mass range from 400 m/z to 2000 m/z every second while the LTQ (Trap) acquired up to 5 MSMS (peptide sequence) spectra in parallel. Data were acquired using the standard Thermo Xcalibur software. MS data (Orbitrap) was stable to 2-3 ppm and a background ion was used for mass drift assessment. MSMS data (LTQ) was measured to approximately 0.6 Da but the parent mass was acquired from the low ppm Orbitrap data. Peptides were eluted from a C18 LC column using triplicate injections to ensure reliability and repeatability of the data. A search file was created from the triplicate injections from each lavage preparation (patient sample) and converted into a MGF (Mascot Generic Format) file using a combination of Xcalibur and Mascot software packages.

Database searching was done using the Mascot search engine (Matrix Science, UK) against the RefSeq database (http://www.ncbi.nlm.nih.gov/RefSeq/) with taxonomy specified as human (*homo sapiens*), a mass accuracy of 10 ppm for the parent ion (MS) and 0.6 Da for the fragment ions (MS/MS), and "no enzyme" selected. Searching without enzyme specificity was performed due to the presence of digestive enzymes in the sample that may modify or truncate peptides being examined. The RefSeq database was supplemented by the addition of antibody sequences that are included in the SwissProt protein database, as these antibody sequences are not part of the standard RefSeq listing.

Higher Mascot scores indicated better proteins hits and were correlated to relative protein levels. A score threshold of ">40" was indicative of a p-value significance of <0.05 as determined by the Mascot scoring system based on the search of this database with no enzyme specificity; a score of 40 is consistent with a p<0.01. Standard Mascot scoring was used whereby only the highest score was added for each peptide detected, even if it was sampled during MS/MS multiple times. For all data included, scores were all >40 in at least one sample per protein line. For additional confidence, the numbers of significant peptides were also reported and a minimum criterion of at least 2 peptides was selected. Very few had less than 3 peptides. All significant peptides counted represented different sequences (individual peptides) from their respective proteins. The score and numbers of significant peptides are reported in the format x/y where x is the score and y the number of significant peptides. Proteins were reported as protein name and the "gi" number defined by the protein database of the NCBI. The sequences contained in each of the "gi" numbers in the NCBI database listed throughout the present application are incorporated herein by reference. Where a protein is named in its preprotein or other non-mature form, the mature form of the protein is equally implied including such changes as removal of signal sequences and the addition of post-translational modifications. Proteins were named by gene derived sequence to provide consistency.

Identification of Polypeptides Associated with Endometrial Cancer

Sample polypeptide data was derived from 306 LC-MS runs from 102 subjects which included 52 Endometrial Cancer (EmCa) patients and 50 normal control subjects. Subject groups were compared to identify promising candidate markers from among 3740 peptides. After normalization and combining replicate runs from each subject, AUC, Wilcoxon rank sum test were computed to evaluate distributional differences between cancer and normal groups. The Wilcoxon test combining with AUC identified 32 peptides exceeding the 5% false discovery rate (FDR) threshold and AUC 0.80. The Wilcoxon procedure was also performed using non-normalized data to assess the effect of the normalization procedure. In this setting, 10 peptides were identified that exceeded the 5% FDR threshold and AUC 0.80.

Data Analysis Approach

Endometrial cancer data was analyzed using the Wilcoxon rank-sum test, Fisher's exact test, fold change, and a ROC curve analysis to identify potentially useful biomarkers. A false discovery rate method was applied to adjust p-values for multiple comparison.

Combining Data and Peptide Selection

Endometrial cancer patients data sets were combined. There were a total of 102 (control: 50, disease: 52) subject samples included in the new data and 42 in old data set each with 3 runs. Among the subjects in old data, 11 subjects were not in new data. Among the disease subjects, 28 had co-existing diagnoses and 24 without co-existing diagnoses. In the new data set there were 6 disease subject samples from surgical patients which were also included in this analysis. After removal of duplicates (multiple MASCOT matches), the new data contain 3740 peptide bins for 306 LC-MS runs (samples from the cervix of patients in the clinic). The old data contain 3931 peptide bins. The samples were grouped into 3 non-disjoint sets for analysis: (1) Old subjects: Subjects in old data set; (2) All subjects: Subjects in new data; and (3) New subjects: Subjects in new data but not in old data. Peptide signals were screened as follows: (1) For the old data set, peptide signals were identified that met the 5% FDR adjusted Wilcoxon test p-value. Seventy (70) signals met this criterion. (2. For the new data set with all subjects, 2615 peptide signals exceeded the 0.05 FDR threshold. This large number was filtered, and only those signals with AUC greater than 0.80 and Wilcoxon test FDR p-value less than 0.01 were selected. (3) For NEW subjects in current data set, 2400 peptide signals exceeded the 0.05 FDR threshold. As above, only those signals with AUC greater 0.80 and Wilcoxon test FDR p-value less than 0.01 were filtered and retained. This still resulted in 115 signals.

LASSO Logistic Regression

Using the Wilcoxon test P-values, the first 100 peptides with smallest p-values as candidate predictors in a classification model were selected for further analysis. These peptide predictors to fit a logistic regression model to classify each subject's disease status. A statistical method known as the Lasso was used to screen potential predictors (Tibshirani, R. (1996). "Regression Shrinkage and Selection via the Lasso" J. Roy. Statist. Soc. Ser. B., 58 (1): 267-288, incorporated by reference in its entirety). Table 10 Table 11, and Table 12 summarize peptides from groups (1) Old subjects, (2) All subjects, and (3) New subjects, respectively, which were further selected using logistic regression through a LASSO selection model. Table 13 summarizes the results for polypeptides identified and associated with endometrial cancer.

TABLE 10

| Mass | Time |
|---|---|
| 922.14 | 67.79 |
| 1016.573 | 33.75 |
| 1041.58 | 32.29 |
| 1383.698 | 43.97 |
| 1860.615 | 69.42 |
| 2384.165 | 36.07 |
| 4618.333 | 68.3 |

TABLE 11

| Mass | Time |
|---|---|
| 1431.608 | 29.81 |
| 2097.006 | 52.97 |
| 3304.741 | 52.19 |

TABLE 12

| Mass | Time |
|---|---|
| 561.775 | 36.97 |
| 1041.58 | 32.65 |
| 1066.509 | 41.81 |
| 2098.006 | 52.99 |
| 5673.911 | 70.26 |

TABLE 13

| Protein ID | Mass | Time | Ions Score | Relative Abundance Patient | Control | Patient/ control | Peptide Sequence | SEQ ID NO |
|---|---|---|---|---|---|---|---|---|
| gi\|4502027: albumin preproprotein | 1012.590 | 42.11 | 100 | 2844101 | 857464 | 3.32 | LVAASQAALGL | 9 |
| gi\|4502027: albumin preproprotein 599-609 | 1066.509 | 41.81 | 64 | 22423 | 1620 | 13.84 | LVAASQAALGL (iron modified) | 9 |
| gi\|4502027: albumin preproprotein | 1341.323 | 52.36 | 101 | 3209793 | 887045 | 3.62 | AVMDDFAAFVEK | 24 |
| gi\|4502027: albumin preproprotein 570-581 | 1395.543 | 52.21 | 69 | 30123 | 926 | 32.52 | AVMDDFAAFVEK (iron modified) | 24 |
| gi\|4502027: albumin preproprotein | 1622.780 | 69.99 | 88 | 1051586 | 246814 | 4.26 | DVFLGMFLYEYAR | 25 |
| gi\|4502027: albumin preproprotein | 1676.699 | 70.59 | 45 | 14324 | 644 | 22.23 | DVFLGMFLYEYAR (iron modified) | 26 |
| gi\|4502027: albumin preproprotein | 1638.928 | 35.12 | 107 | 6924100 | 2167818 | 3.19 | KVPQVSTPTLVEVSR | 12 |
| gi\|4502027: albumin preproprotein | 2044.088 | 53 | 95 | 9857009 | 2941608 | 3.35 | VFDEFKPLVEEPQNLIK | 11 |
| gi\|4502027: albumin preproprotein 397-413 | 2098.006 | 52.99 | 63 | 326795 | 23125 | 14.13 | VFDEFKPLVEEPQNLIK (iron modified) | 11 |
| gi\|4502027: albumin preproprotein | 2403.166 | 77.28 | 101 | 1298127 | 506303 | 2.56 | MPCAEDYLSVVLNQLCVLHEK | 27 |
| gi\|4502027: albumin preproprotein | 2457.083 | 77.27 | 58 | 11463 | 1692 | 6.78 | MPCAEDYLSVVLNQLCVLHEK (iron modified) | 27 |
| gi\|4502027: albumin preproprotein | 2413.048 | 34.27 | 78 | 2944240 | 615976 | 4.78 | VHTECCHGDLLECADDRADLAK | 28 |
| gi\|4502027: albumin preproprotein | 2466.963 | 34.63 | 52 | 11226 | 655 | 17.15 | VHTECCHGDLLECADDRADLAK (iron modified) | 28 |
| gi\|4502027: albumin preproprotein | 2541.270 | 61.1 | 107 | 623866 | 172989 | 3.61 | QNCELFEQLGEYKFQNALLVR | 29 |
| gi\|4502027: albumin preproprotein | 2595.190 | 61.93 | 42 | 8910 | 250 | 35.61 | QNCELFEQLGEYKFQNALLVR (iron modified) | 29 |
| gi\|4502027: albumin preproprotein | 2559.277 | 74.12 | 77 | 1206784 | 181128 | 6.66 | RMPCAEDYLSVVLNQLCVLHEK | 30 |
| gi\|4502027: albumin preproprotein | 2613.185 | 74.37 | 48 | 23721 | 4622 | 5.13 | RMPCAEDYLSVVLNQLCVLHEK (iron modified) | 30 |

TABLE 13 -continued

| Protein ID | Mass | Time | Ions Score | Relative Abundance Patient | Control | Patient/ control | Peptide Sequence | SEQ ID NO |
|---|---|---|---|---|---|---|---|---|
| gi\|4502027: albumin preproprotein | 2720.327 | 51.22 | 74 | 4403200 | 2491217 | 1.77 | LVRPEVDVMCTAFHDNEETFLKK | 31 |
| gi\|4502027: albumin preproprotein | 2774.248 | 51.08 | 43 | 30582 | 4377 | 6.99 | LVRPEVDVMCTAFHDNEETFLKK (iron modified) | 31 |
| gi\|4502027: albumin preproprotein | 2916.320 | 61.65 | 114 | 2853173 | 1195016 | 2.39 | SHCIAEVENDEMPADLPSLAADFVESK | 32 |
| gi\|4502027: albumin preproprotein 311-337 | 2970.239 | 61.7 | 93 | 128088 | 28061 | 4.57 | SHCIAEVENDEMPADLPSLAADFVESK (iron modified) | 32 |
| gi\|4502027: albumin preproprotein | 3361.519 | 61.31 | 120 | 870294 | 46338 | 18.78 | SHCIAEVENDEMPADLPSLAADFVESKDVCK | 33 |
| gi\|4502027: albumin preproprotein | 3415.437 | 62.44 | 48 | 64125 | Not detected | Greater than 100 | SHCIAEVENDEMPADLPSLAADFVESKDVCK (iron modified) | 33 |

Example 4—Identification of Polypeptides Associated with Ovarian Cancer

Identification of Polypeptides

Candidate polypeptides were identified from samples by mass spectrometry as described in Example 3.

Identification of Polypeptides Associated with Ovarian Cancer

Sample peptides from 249 LC-MS runs from 83 subjects which included 33 ovarian cancer (OVCA) patients and 50 normal control subjects were evaluated. Biomarker study subject groups were compared to identify promising candidate markers among 2942 peptides. After normalization and combining replicate runs from each subject, AUC, Wilcoxon rank sum test were computed to evaluate distributional differences between cancer and normal groups. The Wilcoxon test identified 357 peptides exceeding the 5% false discovery rate (FDR) threshold. The Wilcoxon procedure was also performed using non-normalized data to assess the effect of the normalization procedure. In this setting, 429 peptides were identified that exceeded the 5% FDR threshold. The peptide lists for normalized and non-normalized data contained 298 common peptides.

Data Analysis Approach

Ovarian cancer data was analyzed using the Wilcoxon rank-sum test, Fisher's exact test, fold change, and a ROC curve analysis to identify potentially useful biomarkers. A false discovery rate method was applied to adjust p-values for multiple comparison.

Combination of Data and Peptide Selection

Ovarian cancer patients data sets were combined. There were a total of 83 (control: 50, disease: 33) subject samples included in a new data and 35 subject samples in old data set each with 3 runs. After removal of duplicate rows (multiple MASCOT matches), the new data contain 2942 peptide bins for 249 LC-MS runs (samples from the cervix of patients in the clinic). The old data contained 5129 peptide bins. The samples were grouped into 3 non-disjoint sets for analysis: (1) Old subjects: Subjects in old data; (2) All subjects: Subjects in new data; and (3) New subjects: Subjects in new data but not in old data. Peptide signals were screened as follows: (1). For the old data set, peptide signals were identified that met the 5% FDR adjusted Wilcoxon test p-value. One hundred twenty seven (127) signals met this criterion. These corresponded to those signals identified previously. Further filtering using AUC greater than 0.75, identified 64 peptide signals. (2) For the new data set with all subjects, 357 peptide signals exceeded the 0.05 FDR threshold. As in old data, further filtering using AUC greater than 0.75, 12 peptide signals were identified. (3) For NEW subjects in the data set, 304 peptide signals exceeded the 0.05 FDR threshold. Here we filtered to retain only those signals with AUC greater 0.75 were filtered, this resulted in 62 signals. Table 14 summarizes the results for polypeptides identified and associated with ovarian cancer.

TABLE 14

| Protein ID | Mass | Time | Ions score | Relative abundance Patient | Control | Patient/ Control | Peptide sequence | SEQ ID NO |
|---|---|---|---|---|---|---|---|---|
| gi\|4502027: albumin preproprotein | 1638.928 | 35.15 | 107 | 4464112 | 2167818 | 2.059 | KVPQVSTPTLVEVSR | 12 |
| gi\|4502027: albumin preproprotein chymotryptic | 998.51 | 66.58 | 43 | 104572 | 34562 | 3.026 | FYAPELLF | 13 |
| gi\|4502027: albumin preproprotein | 2044.088 | 52.9 | 95 | 5258510 | 2941741 | 1.788 | VFDEFKPLVEEPQNLIK | 11 |

TABLE 14-continued

| Protein ID | Mass | Time | Ions score | Relative abundance Patient | Control | Patient/Control | Peptide sequence | SEQ ID NO |
|---|---|---|---|---|---|---|---|---|
| gi\|4502027: albumin preproprotein | 1341.627 | 52.17 | 101 | 2030263 | 887045 | 2.289 | AVMDDFAAFVEK | 14 |
| gi\|4502027: albumin preproprotein semi-tryptic | 1395.797 | 42.7 | 88 | 67373 | 386 | 174.389 | KVPQVSTPTLVEV | 15 |
| gi\|4502027: albumin preproprotein | 1148.606 | 33.5 | 74 | 1537722 | 890088 | 1.728 | LVNEVTEFAK | 16 |
| gi\|4502027: albumin preproprotein semi-tryptic | 1404.715 | 49.93 | 48 | 395828 | 13855 | 28.57 | RHPYFYAPELL | 17 |
| gi\|4502027: albumin preproprotein semi-tryptic | 1756.898 | 40 | 94 | 214352 | 270 | 792.761 | EDHVKLVNEVTEFAK | 18 |
| gi\|4502027: albumin preproprotein | 2098.007 | 52.79 | 63 | 102806 | 23125 | 4.446 | VFDEFKPLVEEPQNLIK (iron modified) | 11 |
| gi\|4502027: albumin | 952.498 | 44.1 | 47 | 192862 | 38163 | 5.054 | YLYEIAR | 19 |
| gi\|4502027: albumin preproprotein semi-tryptic | 1168.575 | 40.96 | 68 | 40211 | 0 | 40211 | NYAEAKDVFL | 20 |
| gi\|4502027: albumin preproprotein semi-tryptic | 1302.737 | 38.63 | 107 | 54048 | 0 | 54048 | AEVSKLLVTDLTK | 21 |
| gi\|4502027: albumin preproprotein + modification | 2070.104 | 61.11 | 76 | 607458 | 493748 | 1.23 | VFDEFKPLVEEPQNLIK | 11 |
| gi\|4502027: albumin 311-337 | 2970.239 | 61.7 | 91 | 37843 | 28061 | 1.349 | SHCIAEVENDEMPADLPSLAADF VESK (iron modified) | 23 |

Example 4—Analysis of Polypeptides Associated with Endometrial Cancer

Albumin peptides previously associated with the presence of endometrial cancer were further analyzed.

Data Source and Processing

The peptides were identified by mass-to-charge ("mass") and retention time ("time"). A total of 32 peptide signals selected from the data set for 306 mass spec runs (102 patient samples). Three LC-MS runs were performed for each patient sample. Peptide peak areas were normalized using the 80th percentile matching described in previous analyses. Peptides with zero peak areas were assumed to be below the limit of quantification (BQL). Zero areas were replaced with ½ the minimum reported peak area for the corresponding peptide. Peak areas were subsequently log 10 transformed, and averaged across the three runs for each patient. Thus, each patient contributes to the data analysis a single (log 10) average peak area for each peptide. Modified-to-unmodified peptide ratios were computed separately for each LC-MS run, after replacement of BQL values. Ratios were subsequently log 10 transformed and averaged for each patient.

Statistical Modeling Approach

As described in Example 1, the methods used for statistical model selection included the "lasso" method with penalty factor chosen by leave-one-out cross-validation LOOCV (with minimum deviance criterion) (Tibshirani, R. (1996). "Regression Shrinkage and Selection via the Lasso" J. Roy. Statist. Soc. Ser. B., 58 (1): 267-288). A secondary method of model selection, best subsets regression, was also used for the different peptide groups.

Albumin Peptides

Six peptides from albumin were selected. The mass/time values for these are shown in Table 15. Peptides at with masses about 2097 and about 2098 are iron modified versions of the peptide with mass about 2044 (SEQ ID NO:11). These are believed to differ only in that they contain differing iron (Fe) isotopes. Similarly, the peptide with mass about 1066 is likely a modified version of the peptide with mass about 1012 (SEQ ID NO:10).

TABLE 15

| Mass | time | SEQ ID NO |
|---|---|---|
| 2098.01 | 52.99 | 11 |
| 2044.09 | 53.00 | 11 |
| 2097.01 | 52.97 | 11 |
| 1066.51 | 41.81 | 10 |
| 1012.59 | 42.11 | 10 |
| 1638.93 | 35.12 | 12 |

Among albumin peptides, an iron (Fe) modified peptide with mass about 2098 (SEQ ID NO:11) was the single best predictor of endometrial cancer. Peptides at masses about 1012 (SEQ ID NO:10), about 1639 (SEQ ID NO:12), and about 2044 (SEQ ID NO:11) were also useful in distinguishing endometrial cancer from control patient samples. The area under the receiver operating characteristic curve (AUC) for this four-predictor model was 0.90.

Modified Peptides

Modified peptides include a set of nine modified peptides were evaluated to identify potential predictors of endometrial cancer. Six of these nine peptides were selected in a logistic regression model. These included peptides with masses about 1213, about 1067 (SEQ ID NO:10), and about 2098 (SEQ ID NO:11). Modified peptides were selected for inclusion in the lasso logistic regression model. All were positively associated with increased probability of endometrial cancer. The peptides included in this collection were strongly associated with separation of control and endometrial cancer patient samples.

Example 5—Analysis of Polypeptides Associated with Ovarian Cancer

Four groups of peptides previously associated with the presence of ovarian cancer were further analyzed. The groups included: albumin peptides; confidently-identified peptides; ANN peptides; and modified peptides. The AUC values ranged from 0.84 to 0.89. Many of the peptide signals were not observed in control samples, and observed in only a portion of ovarian cancer cases. It is unclear whether these peptides were absent from affected samples, or present but below detection limits.

Data Source and Processing

The peptides to be further evaluated were identified by mass-to-charge ("mass") and retention time ("time"). A total of 36 peptide signals selected from the data set for 306 mass spec runs (102 patient samples). Three LC-MS runs were performed for each patient sample. Peptide peak areas were normalized using the 80th percentile matching described in previous analyses. Peptides with zero peak areas were assumed to be below the limit of quantification (BQL). Zero areas were replaced with ½ the minimum reported peak area for the corresponding peptide. Peak areas were subsequently log 10 transformed, and averaged across the three runs for each patient. Thus, each patient contributes to the data analysis a single (log 10) average peak area for each peptide. Modified-to-unmodified peptide ratios were computed separately for each LC-MS run, after replacement of BQL values. Ratios were subsequently log 10 transformed and averaged for each patient.

Statistical Modeling Approach

The primary method used for statistical model selection was the "lasso" as described in Example 1.

Albumin Peptides

Thirteen peptides from albumin were evaluated. These are listed in Table 16.

TABLE 16

| Mass | time | SEQ ID NO |
|---|---|---|
| 952.50 | 44.10 | 19 |
| 998.51 | 66.58 | 13 |
| 1148.61 | 33.50 | 16 |
| 1168.58 | 40.96 | 20 |
| 1302.74 | 38.63 | 21 |
| 1341.63 | 52.17 | 14 |
| 1395.80 | 42.70 | 15 |
| 1404.71 | 49.93 | 17 |
| 1638.93 | 35.15 | 12 |
| 1756.90 | 40.00 | 18 |
| 2044.09 | 52.90 | 11 |
| 2070.10 | 61.11 | 11 |
| 2098.01 | 52.79 | 11 |

The 13 peptides were evaluated as potential predictors. Although several of these peptides were related through post-translational modifications (e.g., peptides at mass about 2097 and about 2098 are iron modified versions of the mass about 2044 peptide (SEQ ID NO:11)), combining peptides did not result in substantial improvement in predictive performance.

Exploratory Analysis

Figure 7:
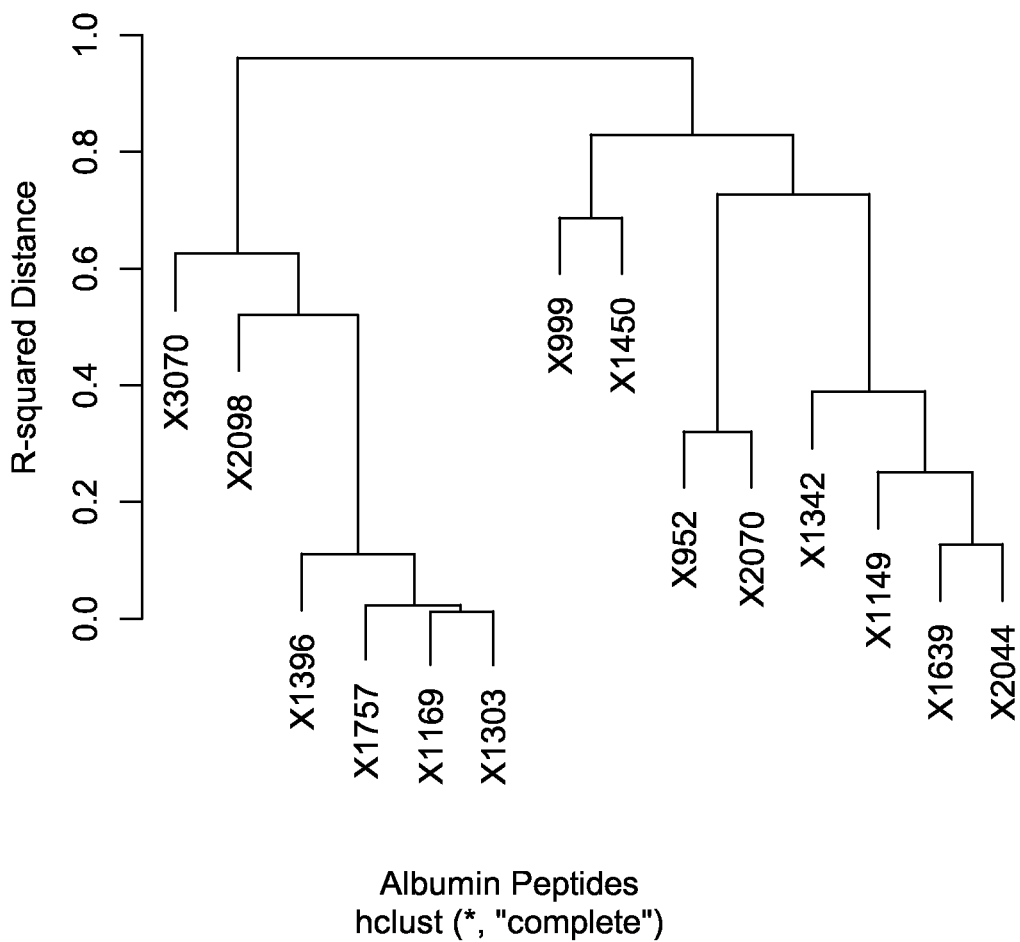
FIG. 7 shows clustering of albumin peptides. Clustering was based on similarity (r2) between albumin peptides. Those peptides that exhibited similar information clustered together. Peptides at masses 1169 (SEQ ID NO:16), 1303 (SEQ ID NO:17), and 1757 (SEQ ID NO:13), provide nearly identical information for any regression analysis.

The relationships between albumin peptides' peak areas ($\log_{10}$ scale, patient means) were evaluated. FIG. 7 shows the results of peptide clustering, where clustering similarity is based on the squared correlation coefficient. Here, $r^2$ was between 0 and 1, with 1 denoting perfect linearity between two peptides. The "R-squared Distance" was computed as $1-r^2$. Thus, an R-squared distance near zero indicated nearly identical information in the two peptides. The cluster dendrogram shows that peptides at masses about 1169 (SEQ ID NO:20), about 1303 (SEQ ID NO:21), and about 1757 (SEQ ID NO:18) were nearly co-linear. This meant that any one of these peptides contained almost the same information as the other two. As a consequence, only one of these three was useful for predictive modeling.

Model Selection Results

The modeling approach selected six peptide signals for predicting ovarian cancer. These signals and their estimated coefficients are shown in Table 17.

TABLE 17

| Polypeptide | Coefficient | Odds factor |
|---|---|---|
| X952 | 0.14 | 1.15 |
| X999 | 0.09 | 1.09 |
| X1405 | 0.44 | 1.56 |
| X2044 | 0.63 | 1.89 |
| X2098 | 0.15 | 1.17 |
| X3070 | 0.95 | 2.59 |

Intercept: −10.22
Modeling results
Null deviance = 111.56
Fitted model dev = 73.32
Difference dev = 38.23
Model p-value = 1.012422e−06
AUC = 0.85

The selected albumin peptides predicted ovarian cancer substantially better than random chance ($p \sim 10^{-6}$). The regression coefficients indicated that increases in any of the selected peptide peak areas were associated with increasing odds of ovarian cancer. The area under the receiver operating characteristic curve (AUC) was 0.85. This was better than random chance.

The best subsets approach was applied to the set of albumin peptide predictors, and identified a statistical model with peptides at masses about 2044 and about 3070 as predictors. The coefficients in the logistical regression model are shown in Table 18. The fitted values from this model results in an AUC value of 0.86. Note that the intercept (−337.77) and X3070 (116.21) have coefficient estimates of large magnitude and large standard errors. This behavior was a consequence of the numerical instability described herein. In deed, for all groups of peptides, the best subsets procedure resulted in this behavior.

TABLE 18

|  | Estimate | Std. Error | z value | PR(>|z|) |
|---|---|---|---|---|
| (Intercept) | −337.77 | 27923.41 | −0.01 | 0.99 |
| X2044 | 1.48 | 0.46 | 3.22 | 0.00 |
| X3070 | 116.21 | 9902.54 | 0.01 | 0.99 |

Modified Peptides

Eight peptides with post-translational modifications were selected for analysis. The mass and retention times are shown in Table 19.

TABLE 19

| Mass | time |
| --- | --- |
| 1294.67 | 39.31 |
| 1430.73 | 36.37 |
| 1494.74 | 29.14 |
| 1534.74 | 41.66 |
| 1825.88 | 50.12 |
| 2226.09 | 39.98 |
| 2566.09 | 56.98 |
| 3069.58 | 21.67 |

The lasso-CV procedure identified the following peptides for inclusion in the statistical model shown Table 20.

TABLE 20

| Peptide | Coefficient | Odds factor |
| --- | --- | --- |
| (Intercept) | −92.95 | |
| X1295 | 7.61 | 2016.67 |
| X1431 | 3.21 | 24.67 |
| X1535 | −0.47 | 0.62 |
| X1826 | 1.89 | 6.59 |
| X2226.1 | −0.77 | 0.46 |
| X3070 | 17.73 | 50216457.72 |

Modeling results
Null deviance −= 111.56
Fitted model dev = 78.03
Difference dev = 33.52
Model p-value = 8.320073e−06
AUC = 0.86

Figure 8:
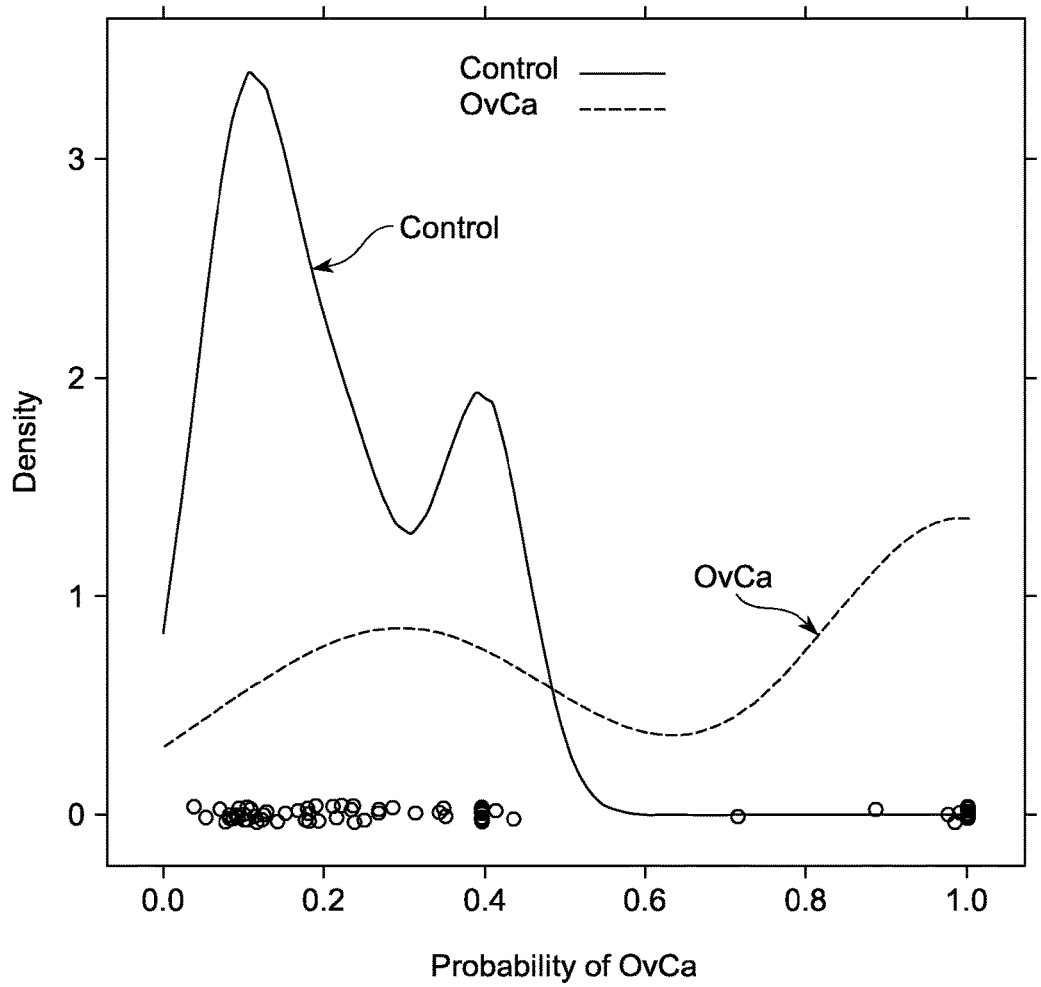
FIG. 8 is a graph showing the distribution of fitted probabilities of ovarian cancer (OvCa) for control and diseases patients. Probability from lasso logistic regression using peptides 1295, 1431, 1535, 1826, 2226, 3070.
Figure 9:
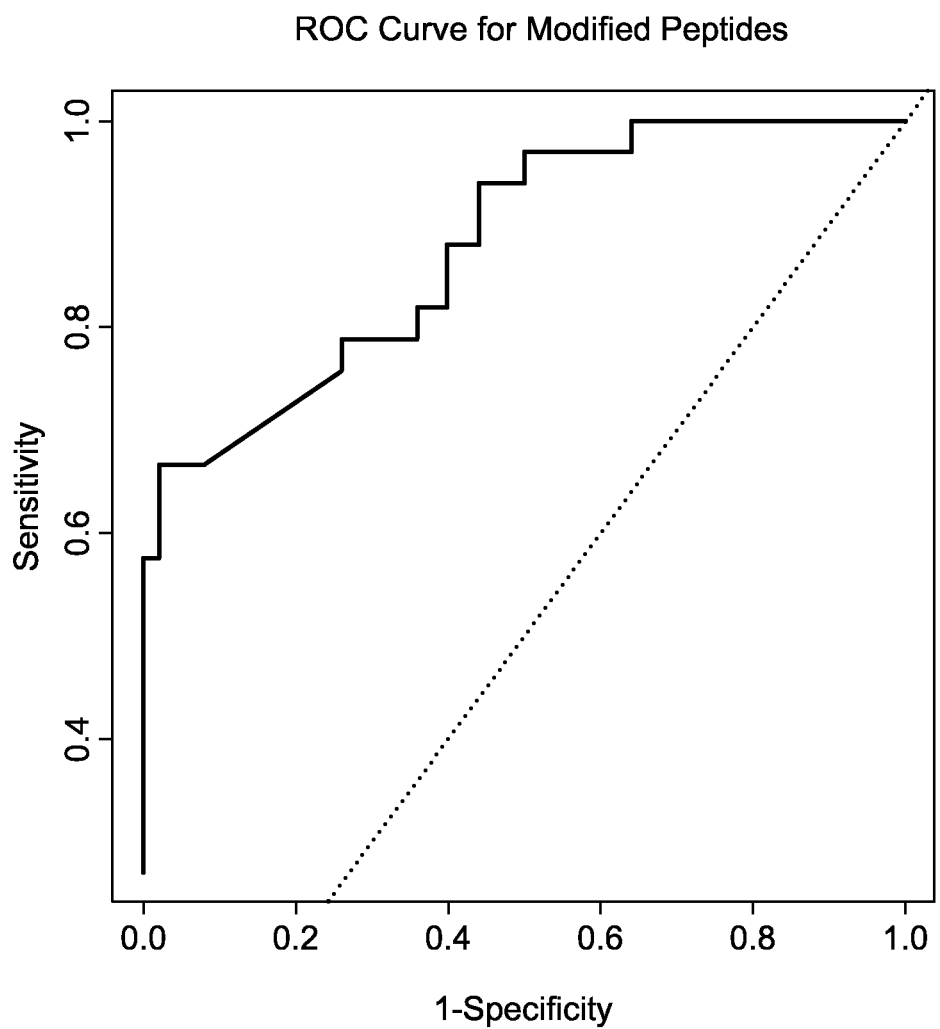
FIG. 9 is a graph showing the receiver operating characteristic curve for control and diseases patients for modified peptides model. The estimated AUC for model estimated probabilities was 0.86.

Six modified peptides were selected for inclusion in the lasso logistic regression model. Four were positively associated with increased probability of ovarian cancer. This collection of peptides was strongly associated with separation of control and ovarian cancer patient samples (p~10e-6), and an AUC of 0.86. FIG. 8 and FIG. 9 illustrate the distributions and ROC curve for model estimated probabilities for control and ovarian cancer patients.

Example 6—Iron-Modified Polypeptides

In addition to the data shown in FIG. 6, spectra from 4 other peptides were searched on mascot using the human NCBI RefSeq database with a modification of iron attachment set. FIG. 10, FIG. 11, FIG. 12, and FIG. 13 show spectra of a polypeptide of mass about 1066 (SEQ ID NO:10); a polypeptide of mass about 1395 (SEQ ID NO:15); a polypeptide of mass about 2098 (SEQ ID NO:11), and a polypeptide of mass about 2970 (SEQ ID NO:23; SHCI-AEVENDEMPADLPSLAADFVESK), respectively. The automated Mascot assignment of the four peptides shown in FIGS. 10-13 all assign to tryptic peptides derived from human albumin (gi:4502027) that were observed to be significantly elevated in cancer. While the position of the attachment was identified in each search, Mascot is not designed for divalent cations and the location could be, within limits, elsewhere on the sequence. The NCBI RefSeq database is gene sequence based and was used for convenience. Pre-sequences were not part of the mature protein in the samples. Masses provided were those identified by DifproWare based on the data form all samples; Mascot search results were form a single MS/MS scan in one sample and are only one of many for each peptide. The peptide of measured mass 1066.5090 was matched to the peptide from amino acids 599-609 which has an iron modified calculated mass of 1066.5110 and an ion score of 55 (FIG. 10). The peptide of measured mass 1395.5430 was matched to the peptide from amino acids 570-581 with an iron modified calculated mass of 1395.5468 and an ion score of 52 (FIG. 11). The peptide of measured mass 2098.0061 was matched to the peptide from amino acids 397-413 with an iron modified calculated mass of 2098.0074 and an ion score of 77 (FIG. 12). The peptide of measured mass 2970.2400 was matched to the peptide from amino acids 311-337 with an iron modified calculated mass of 2970.2350 and an ion score of 91 (FIG. 13).

Example 7—Production of Antibodies

Antibodies or fragment thereof, capable of specifically recognizing polypeptides provided herein, for example polypeptides comprising SEQ ID NOs.:9-33, may be generated by a variety of methods well known in the art. In an example, a nucleic acid encoding a polypeptide comprising one of comprising SEQ ID NOs.:9-33 or fragment thereof, is cloned into an expression vector and the polypeptide expressed in a cell. The expressed polypeptide can be enriched or purified from the cell by a variety of methods. In an example, the expression vector provides a cleavable His tag at one end of the expressed polypeptide. The polypeptide comprising the His tag can be purified using a nickel affinity column. The His tag is cleaved from the polypeptide. The polypeptide can be used to produce antibodies.

Monoclonal antibodies can be produced by well known hybridoma fusion technology. For example, monoclonal antibody to epitopes of any of the polypeptides isolated as described can be prepared from murine hybridomas according to the classical method of Kohler, G. and Milstein, C., Nature 256:495 (1975) or derivative methods thereof. Briefly, a mouse is repetitively inoculated with a few micrograms of the selected protein or peptides derived therefrom over a period of a few weeks. The mouse is then sacrificed, and the antibody producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as Elisa, as originally described by Engvall, E., Meth. Enzymol. 70:419 (1980), and derivative methods thereof. Selected positive clones can be expanded and their monoclonal antibody product harvested for use. Detailed procedures for monoclonal antibody production are described in Davis, L. et al. Basic Methods in Molecular Biology Elsevier, New York. Section 21-2.

Polyclonal antibodies can be produced by methods well known in the art. For example, Polyclonal antiserum containing antibodies to heterogenous epitopes of a single protein can be prepared by immunizing suitable animals with the expressed protein or peptides derived therefrom described above, which can be unmodified or modified to enhance immunogenicity. Effective polyclonal antibody production is affected by many factors related both to the antigen and the host species. For example, small molecules tend to be less immunogenic than others and may require the use of carriers and adjuvant. Also, host animals vary in response to site of inoculations and dose, with both inadequate or excessive doses of antigen resulting in low titer antisera. Small doses (ng level) of antigen administered at multiple intradermal sites appears to be most reliable. An effective immunization protocol for rabbits can be found in Vaitukaitis, J. et al. J. Clin. Endocrinol. Metab. 33:988-991 (1971). Booster injections can be given at regular intervals, and antiserum harvested when antibody titer thereof, as determined semi-quantitatively, for example, by double immunodiffusion in agar against known concentrations of the antigen, begins to fall. See, for example, Ouchterlony, O. et al., Chap. 19 in: Handbook of Experimental Immunology D. Wier (ed) Blackwell (1973). Plateau concentration of antibody is usually in the range of 0.1 to 0.2 mg/ml of serum (about 12 .mu.M). Affinity of the antisera for the antigen is determined by preparing competitive binding curves, as described, for example, by Fisher, D., Chap. 42 in: Manual of Clinical Immunology, 2d Ed. (Rose and Friedman, Eds.) Amer. Soc. For Microbiol., Washington, D.C. (1980).

Antibody preparations prepared according to either protocol are useful in quantitative immunoassays which determine concentrations of antigen-bearing substances in biological samples; they are also used semi-quantitatively or qualitatively to identify the presence of antigen in a biological sample. The antibodies may also be used in therapeutic compositions for killing cells expressing the protein or reducing the levels of the protein in the body.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

What is claimed is:

1. A method for determining the level of at least one polypeptide in a sample from a female subject suspected of having endometrial cancer, the method comprising:
   obtaining a sample from the subject, wherein the sample is obtained from the cervix, the vagina, or the posterior vaginal fornix; and
   determining the level of at least one polypeptide in a sample from said subject, wherein said at least one polypeptide is an albumin protein fragment selected from the group consisting of:
   an albumin protein fragment having a mass about 2044 Da and an iron-modified albumin protein fragment having a mass about 2098 Da, each fragment comprising a polypeptide sequence of SEQ ID NO:11,
   an iron-modified albumin protein fragment having a mass about 2098 Da and comprising a polypeptide sequence of SEQ ID NO:11, an albumin protein fragment having a mass about 1013 Da and an iron-modified albumin protein fragment having a mass about 1067 Da, each fragment comprising a polypeptide sequence of SEQ ID NO:10, an iron-modified albumin protein fragment having a mass about 1067 Da and comprising a polypeptide sequence of SEQ ID NO:10, an albumin protein fragment having a mass about 1639 Da and comprising a polypeptide sequence of SEQ ID NO:12, and an iron-modified albumin protein fragment having a mass about 2098 Da and comprising a polypeptide sequence of SEQ ID NO:11, and an albumin protein fragment having a mass about 1639 Da and comprising a polypeptide sequence of SEQ ID NO:12, and an iron-modified albumin protein fragment having a mass about 1067 Da and comprising a polypeptide sequence of SEQ ID NO:10, wherein the at least one polypeptide has said mass when said sample is digested with trypsin and the mass of said polypeptide is measured using an orbitrap mass spectrometer, wherein said determining the level of said at least one polypeptide comprises a process selected from the group consisting of an immunoassay, a colorimetric assay, a Western blot, an enzyme-linked immunoabsorbent assay (ELISA), a radioimmunoassay, and mass spectrometry.

2. The method of claim 1, further comprising determining the level of an iron-modified albumin protein fragment having a mass about 2098 Da and comprising a polypeptide sequence of SEQ ID NO:11, and an iron-modified albumin protein fragment having a mass about 1067 Da and comprising a polypeptide sequence of SEQ ID NO:10.

3. The method of claim 1, wherein the sample is obtained from a cervical pap specimen.

4. The method of claim 1, wherein the sample is substantially free of cells.

5. The method of claim 1, wherein the polypeptide comprises at least one residue associated with iron.

6. The method of claim 1, wherein said at least one polypeptide is an albumin protein fragment having a mass about 2044 Da and an iron-modified albumin protein fragment having a mass about 2098 Da, each fragment comprising a polypeptide sequence of SEQ ID NO:11.

7. The method of claim 1, wherein said at least one polypeptide is an iron-modified albumin protein fragment having a mass of about 2098 Da and comprising a polypeptide sequence of SEQ ID NO:11.

8. The method of claim 1, wherein said at least one polypeptide is an albumin protein fragment having a mass about 1013 Da and an iron-modified albumin protein fragment having a mass about 1067 Da, each fragment comprising a polypeptide sequence of SEQ ID NO:10.

9. The method of claim 1, wherein said albumin protein fragment is an iron-modified albumin protein fragment having a mass of about 1067 Da and comprising a polypeptide sequence of SEQ ID NO:10.

10. The method of claim 1, wherein said at least one polypeptide is selected from an albumin protein fragment having a mass about 1639 Da and comprising a polypeptide sequence of SEQ ID NO:12, and an iron-modified albumin protein fragment having a mass about 2098 Da and comprising a polypeptide sequence of SEQ ID NO:11; or an albumin protein fragment having a mass about 1639 Da and comprising a polypeptide sequence of SEQ ID NO:12, and an iron-modified albumin protein fragment having a mass about 1067 Da and comprising a polypeptide sequence of SEQ ID NO:10.

11. The method of claim 1, wherein the process comprises:
applying said sample to a solid phase test strip or flow-through test strip comprising an agent which selectively binds to said at least one polypeptide or fragment thereof; and
detecting said polypeptide bound to said agent on said solid phase test strip or flow-through test strip.

12. The method of claim 11, wherein said agent comprises an antibody or fragment thereof.

* * * * *